United States Patent [19]
Okano et al.

[11] Patent Number: 5,820,373
[45] Date of Patent: Oct. 13, 1998

[54] CLEANING DEVICE FOR PERIODONTAL POCKET

[75] Inventors: Koichi Okano, 11-24, Takadacho, Nagahama-shi, Shiga-ken 526; Tsuguo Matsui, Kyoto; Michihisa Sugimoto, Higashiosaka; Masaharu Kita; Takashi Morita, both of Takatsuki; Tomoko Asai, Osaka, all of Japan

[73] Assignee: Koichi Okano, Shiga-Ken, Japan

[21] Appl. No.: 750,469

[22] PCT Filed: Sep. 29, 1995

[86] PCT No.: PCT/JP95/01986

§ 371 Date: Dec. 13, 1996

§ 102(e) Date: Dec. 13, 1996

[87] PCT Pub. No.: WO96/10372

PCT Pub. Date: Nov. 4, 1996

[30] Foreign Application Priority Data

Aug. 29, 1995 [JP] Japan .................................. 7-220487

[51] Int. Cl.⁶ ...................................................... A61G 17/02
[52] U.S. Cl. .............................. 433/80; 433/85; 433/216; 601/162
[58] Field of Search .................................... 433/80, 85, 87, 433/216; 601/162, 163, 165

[56] References Cited

U.S. PATENT DOCUMENTS

| | | |
|---|---|---|
| 3,164,153 | 1/1965 | Zorzi ........................................ 433/216 |
| 3,863,628 | 2/1975 | Vit ............................................. 433/216 |
| 4,108,178 | 8/1978 | Betush ....................................... 433/80 |
| 4,214,871 | 7/1980 | Arnold ....................................... 433/216 |
| 4,906,187 | 3/1990 | Amadera .................................... 433/80 |
| 4,975,054 | 12/1990 | Esrock ....................................... 433/80 |

FOREIGN PATENT DOCUMENTS

| | | |
|---|---|---|
| 56-49608 | 11/1981 | Japan . |
| 64-63671 | 3/1989 | Japan . |
| 568689 | 3/1993 | Japan . |

Primary Examiner—John J. Wilson
Attorney, Agent, or Firm—Armstrong, Westerman, Hattori, McLeland & Naughton

[57] ABSTRACT

A periodontal pocket cleaning device is provided which has a very excellent effect for the prevention of periodontal diseases, which is least liable to cause injury to the periodontal pocket, which can be used at any place without limiting the place of its use, which is able to obtain a stabilized atomized jet without being influenced by the height position of the handy probe, and which is available at a low cost. The periodontal cleaning device includes a handy probe provided with an air-jet ejection mechanism, an air pump for producing compressed air, and an air-feeding tube for feeding the compressed air from the air pump to the handy probe. The handy probe is provided with a liquid storage tank for storing liquid agent such as water or liquid chemicals therein. The jet-out pressure of the compressed air to be ejected from the nozzle of the handy probe is set in a range of from 0.05 to 0.08 kg/cm². The jet-out quanity of the compressed air is set in a range of from 2 to 30 l/min. and the jet-out quanity of the liquid agent is set in a range of from 1 to 10 cc/min.

17 Claims, 27 Drawing Sheets

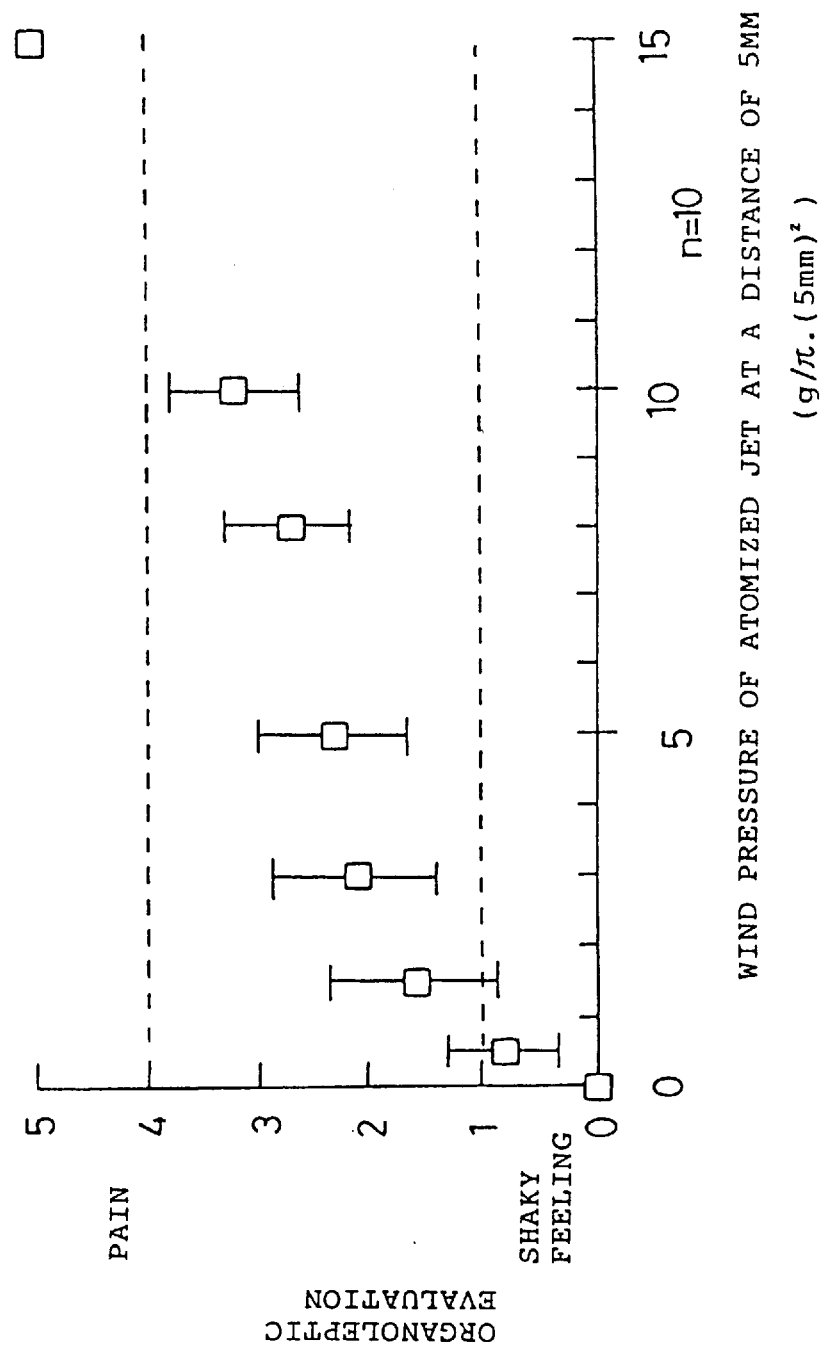

FIG. 23
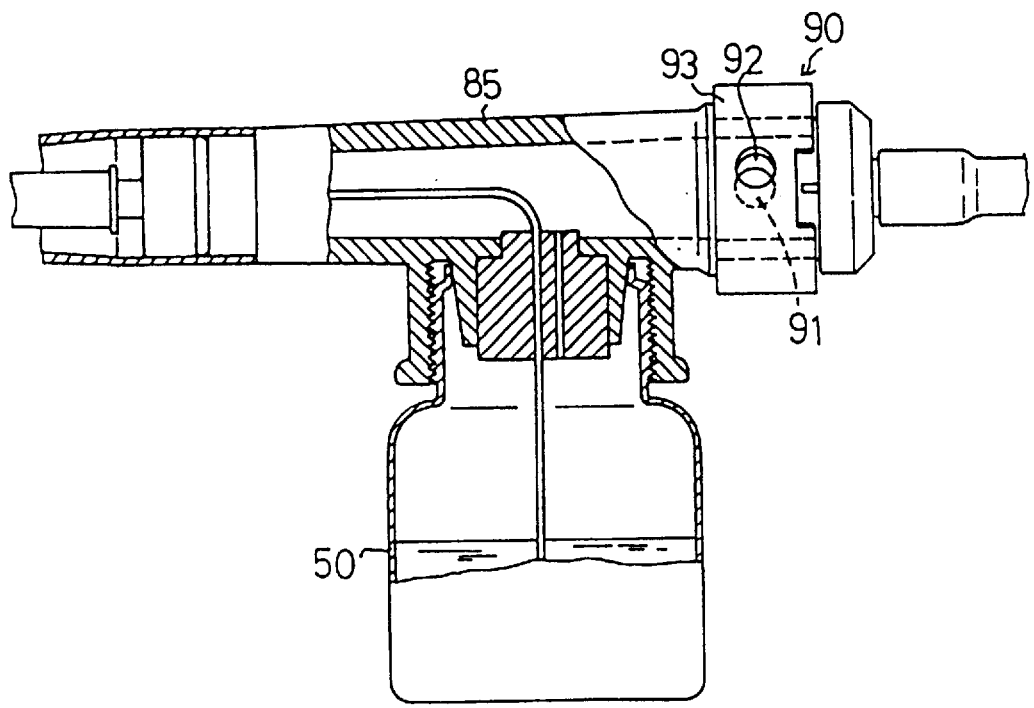
FIG. 24(a)
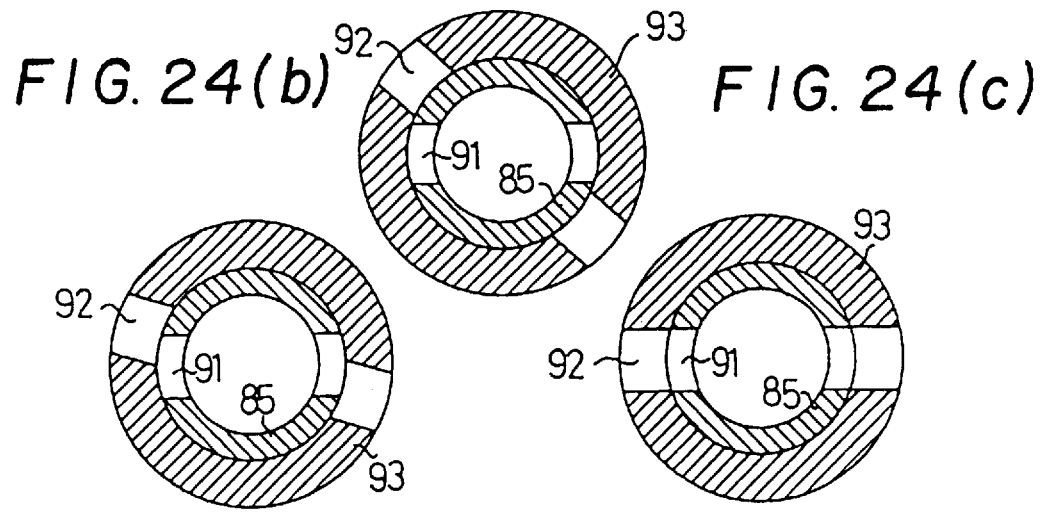
FIG. 24(b)   FIG. 24(c)

FIG. 27(a)
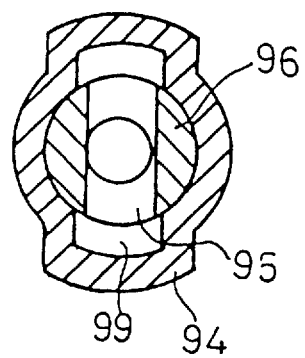
FIG. 27(b)
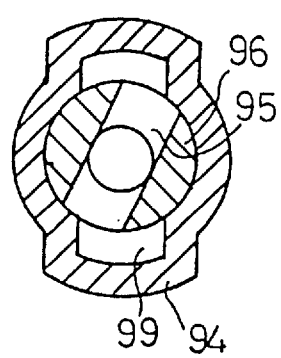
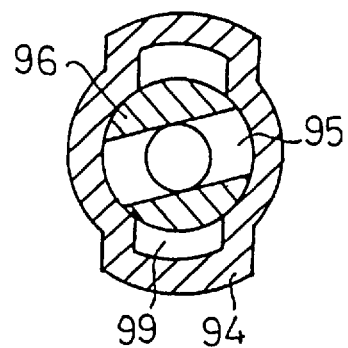
FIG. 27(c)

CLEANING DEVICE FOR PERIODONTAL POCKET

BACKGROUND OF THE INVENTION

1. Field of the Invention

The present invention is concerned with a cleaning device for a periodontal pocket which is capable of carrying out sterilization of pathogenic fungi of periodontal diseases in a safe and easy manner, and with which the therapeutic treatment for improving the conditions of the periodontal pocket can be done not only at dental clinics, but also at ordinary homes in general.

2. Description of the Related Art

It has been known that, when the pathogenic fungi of periodontal diseases propagate in the periodontal pocket existing between the teeth and the gum (or gingiva), dental plaque accumulates, which is the cause of the gingivitis, accumulates. As shown in FIG. 35 of the accompanying drawing, the periodontal pocket is present at a position slightly deeper than the surface 400 of the tooth gum. Since the gum surface 400 is in tight contact with the tooth surface 401, it is usually not possible to clean the interior of the periodontal pocket 402 with a tooth brush and hence, the propagation of periodontal pathogenic fungi and/or accumulation of dental plaque is difficult to suppress.

As a method for suppressing the propagation of pathogenic fungi and/or accumulation of dental plaque in the periodontal pocket, the following three methods have been well known:

1) a method, by which a needle-shaped tool is forced into the periodontal pocket to feed liquid chemicals, such as fungicide, disinfectant, quenching agent, and so forth, thereinto, or to clean the interior of the pocket;

2) a method, by which use is made of a liquid agent injecting nozzle with rubber tip attached to a tip end thereof, and by positioning the rubber tip into the periodontal pocket, the liquid chemicals are injected into the pocket to wash the interior of the pocket; and 3) a method, by which use is made of a device for spouting a pressurized jet water current to wash away the dental plaque therewith.

The first method is steady and effective, but such treatment can only be done by dentists, because of the risk of injury to the gum and hence, it is not a method that can be done at home by an ordinary person for himself or herself.

The second method can be done by a person at home, but it is difficult to position the rubber tip accurately into the periodontal pocket and there may be further problems, such as the liquid chemicals scattering around, making it difficult to inject a sufficient amount of the chemicals into the pocket. In addition, the surrounding area is polluted with the scattered chemicals and hence, the method is problematic.

The third method can be done by any person at home, but has the problem that it is difficult to force the jet water current into the periodontal pocket, even if the water pressure is increased, because the pocket is tightly closed by the gum surface which is in close contact with the tooth surface and hence, the plaque-removing effect is not very good.

For solving the above-mentioned problems to a certain extent, a technique is proposed in Japanese Utility Model Publication No. 4-4733 (hereinafter JP '733). According to the technique of JP '733, a periodontal pocket cleaning device is disclosed which has a construction including: a stationary type main body device, which accommodates integrally therein, an injection nozzle hand-piece having an injection nozzle provided at a tip end thereof; an air-pump to supply pressurized air to the injection nozzle hand-piece; a water tank for storing a large quantity of water therein; and a coaxial double-structured tube for supplying both pressurized air and water to the injection nozzle hand-piece, wherein the spouting pressure of the compressed air from the tip end of the nozzle is set in a range of from 1 to 2 $kg/cm^2$, the spouting quantity of the compressed air is set in a range of from 6 to 9 l/min., and the jet-out quantity of water is set in a range of form 10 to 30 cc/min. JP '733 further describes that, by spouting water and compressed air simultaneously from the tip end of the injection nozzle of the cleaning device, an atomized jet is produced which contains a large quantity of water. The entrance to the periodontal pocket is opened by the wind pressure of the atomized jet and at the same time, by forcing the large quantity of water contained in the atomized jet into the pocket, dental plaque, remnants of food, as well as various bacteria, can be removed from the pocket, with the additional effect that the tooth gum is massaged by the spouting pressure of the atomized jet.

Since the technique of JP '733 produces the atomized jet by mixing a large quantity of water with the compressed air at the tip end of the nozzle, and also forcibly opens the entrance of the periodontal pocket due to the pressure exerted by the atomized jet against the surface of the tooth gum 400, the pocket can be more readily opened than by the conventional jet water current. Hence, the atomized jet cleaning is better than the jet water cleaning with respect to the plaque-removing effect and the pocket-cleaning effect. However, the technique of JP '733 still has the problem that, from the standpoint of disinfection of the pathogenic fungi, the results of the technique are somewhat inferior to the results attained by physically removing plaque and cleaning the tooth gum with the use of various removing tools, or the results attained by doses of chemicals injected into the periodontal pocket by a dentist. Additionally, other problems to be solved still exist.

First, since a principle aim of the technique of JP '733 to wash-away the dental plaque containing the periodontal pathogenic fungi therein, as well as any leftovers of food, by means of the atomized jet containing a large quantity of water therein, a large quantity of water and a highly pressurized air are required. The requirement of a large quantity of water and a highly pressurized air forces an increase in the volume of the water storage tank to be installed in the stationary type main body device. Also, the technique of JP '733 has the further problem that, in order for such a large quantity of water stored in the main body device to be sent out through the coaxial double-structured tube to the injection nozzle hand-piece separated from the main body device by a fair distance, the air-pressure pressure in the vicinity of the tip end of the jet nozzle must be rendered negative to enable water to be sucked up to a level closer to the proximity of the tip end of the jet nozzle. Because the air-pressure must be rendered negative, an air pump having a large delivery pressure is necessary and thus, increases the cost and size of the cleaning device, which is undesirable since size-reduction and price-reduction in such a device is a goal.

Moreover, in order to increase the pocket-cleaning effect with the method of JP '733, the only alternative is to increase the water-feeding quantity with a simultaneous increase in the pressure of the air. An increase in both the water-feeding quantity and the air pressure could cause injury to the delicate inner wall of the periodontal pocket because of excessive pressure of the jet water current.

A still further problem with the technique of JP '733 is that, since a large quantity of water is to be fed into the patient's oral cavity, the water staying in the patient's mouth needs to be disgorged frequently until the end of the cleaning operation. In addition, since the water collected in the patient's mouth tends to be dripped outside of the oral cavity, the place for use of the cleaning device is limited to a wash-stand, etc. In other words, the cleaning device cannot be used at the patient's bed side and hence, the place for use of the cleaning device cannot be chosen freely which is undesirable since it is preferred to be able to use the cleaning device anywhere.

Also, in view of the fact that the water stored in the main body device is conducted to the injection nozzle hand-piece through a long tube, there is also a problem that, when the relationship in height between the injection nozzle hand-piece and the main body device varies, the blow-out quantity of the atomized jet from the hand-piece varies and consequently, there is an inability to inject the atomized jet in a stable manner.

The present invention has been made in view of the above-described problems of the related art and the present invention aims to provide a periodontal pocket cleaning device which: has an extremely superior effect in the prevention of periodontal disease without apprehension of injury to the periodontal pocket; is able to be used anywhere without limitation to the place for its use; is able to obtain a stable atomized jet without being affected by the height of the hand-piece; and can be obtained at a low cost.

SUMMARY OF THE INVENTION

As the result of repeated studies for solving the above-described problems, the present inventors have obtained the following concept. That is to say, the inventor considers that, as a method for preventing periodontic disease, a method that emphasized the disinfection of the pathogenic fungi might be used, in contrast to the above-described method of JP '733, which emphasizes washing out dental plaque or pathogenic fungi, which is the cause of the dental plaque. Furthermore, the inventors firmly believed that the above-mentioned concept could be realized, if a device of a structure for supplying a greater quantity of air into the periodontic pocket could be provided, because the pathogenic fungi of periodontal disease is an anaerobic bacteria and thus, can prevent the oral cavity from being dried out due to the injection of air.

The periodontal pocket cleaning device, according to the present invention, differs from the device of JP '733 in that, it is necessary to find appropriate ranges of the blow-out quantity of compressed air, the injection pressure of the compressed air, and the injection quantity of the water.

Through various experiments, the present inventors conducted research and did studies on the appropriate ranges of the blow-out quantity of compressed air, the injection pressure of the compressed air, and the jet-out quantity of the water. As a result of their research and studies, the present inventors came to the conclusion that the blow-out quantity of the compressed air required for the periodontic pocket cleaning device, as proposed by the present invention, was much larger than the blow-out quantity of the compressed air required by JP '733, while it was necessary to decrease the injection quantity of water from that of JP '733. It was also verified that, from the standpoint of harmfulness to the dental gum, the lower the injection pressure of the compressed air was, the better, and that the pressure of the compressed air of JP '733 was too forceful.

The periodontal pocket cleaning device of the present invention, which is based on what was learned from the inventor's research and studies, has the construction, as follows: a handy probe provided with an air-jet injection mechanism; an air pump for producing compressed air; and an air-feeding tube for sending compressed air to the handy probe.

The handy probe includes: an injection nozzle provided with an injection port at a tip end thereof; a liquid storage tank for storing a liquid agent, such as water or liquid chemicals; a liquid agent guide passage for guiding the liquid agent in the liquid storage tank to approximately the center position of the injection port, via the injection nozzle; and a compressed air guide passage for guiding the compressed air, to be fed outside, to a position surrounding the liquid agent guide passage at the injection port, via the injection nozzle.

The pressure of the compressed air to be blown out of the nozzle of the handy probe is set in a range of from 0.05 to 0.80 kg/cm$^2$. The blow-out quantity of the compressed air is set in a range of from 2 to 30 l/min., and the injection quantity of the liquid agent is set in a range of from 1 to 10 cc/min.

Here, the pressure of the compressed air to be blown out of the nozzle of the hand probe is expressed in terms of the pressure in the interior of the air-feeding tube. The pressure range of 0.05 to 0.8 kg/cm$^2$ gives the value, as measured, in the intermediate part of the air-feeding tube.

The liquid agent guide passage is constructed with: a liquid agent feed-pipe for guiding the liquid agent from the liquid storage tank to the inlet part of the injection nozzle; and an intra-nozzle liquid conduit pipe for guiding the liquid agent to substantially the center position of the jet-out port by coaxially passing through the internal space of the injection nozzle with respect to the outer cylinder of the nozzle.

The compressed air guide passage can be constructed with: an extra-nozzle air feed passage for leading the compressed air to be fed from outside to the injection nozzle; and an intra-nozzle air feed passage for leading the compressed air, led into the injection nozzle up to the injection port, in a manner to coaxially surround the intra-nozzle liquid conduit pipe.

In this case, it is preferable that the compressed air guide passage be branched, and one of the branched compressed air guide passages be guided to the injection nozzle, while the other branched compressed air guide passage be guided into the interior space of the liquid storage tank to pressurize the liquid surface of the liquid agent.

The handy probe is of such a construction that the injection nozzle is associated with the cylindrical part which constitutes the main body of the handy probe. The liquid storage tank, in one case, is integrally joined with the cylindrical part of the handy probe, and in another case, is separately constructed from the cylindrical part of the handy probe, wherein the cylindrical part of the handy probe is connected to the liquid storage tank by means of a connecting tube.

The terminal end of the liquid agent guide passage and the terminal end of the compressed air guide passage face the jet-out port, where a difference obtained by subtraction of the area of the terminal end part if the liquid guide passage from the area if the jet-out port becomes the area of the terminal end part of the compressed air guide passage (i.e., the effective area of the air jet-out part). There is an optimum range for the area of the air jet-out part and the preferred range thereof is from 0.5 mm$^2$ to 20 mm$^2$. The wind pressure at a spot 5 mm distant from the injection port, along the axial direction of the injection nozzle, is in a range of from 1 to 10 g/π•(5 mm)$^2$.

Also, at least a part of the liquid agent guide passage to be positioned at the jet-out port of the handy probe, may be constructed with a flexible tube. The end position of the flexible tube, to be situated at the open center position of the jet-out port, should preferably be is a range of ±2 mm in the axial direction of the nozzle with respect to the outer cylinder of the nozzle.

Further, a diaphragm type compressor may be adopted for the air pump, and for a driving source of the diaphragm and it is preferable to use a reciprocal vibratory body, for a driving source of the diaphragm, to make use of the repulsion-attraction function of electromagnets and permanent magnets.

Various types of adjusting means for the jet-out quantity of the atomized jet may be used. For example, the adjusting means can be realized by providing means for regulating the flow rate of the compressed air in the compressed air guide passage of the handy probe, or at an intermediate part of the air-feed tube for supplying compressed air from the air pump to the handy probe.

As another example, in either the compressed air guide passage of the handy probe, or in an intermediate part of the air-feeding tube for supplying the compressed air to the handy probe, means may be provided for discharging a part of the compressed air to either the outside of the compressed air guide passage or to the outside of the air-feeding tube.

It is also possible to make the nozzle part separable from either the main body of the handy probe, or the intra-nozzle liquid conduit pipe separable from the handy probe main body. It may be feasible that the injection nozzle and the intra-nozzle liquid conduit pipe are integrally fixed in advance.

The periodontal pocket cleaning device of such construction can be used in such a manner that the liquid agent, containing water or liquid chemicals therein, is first fed into the liquid storage tank of the handy probe, followed by operation of the air pump. After a lapse of 1 to 2 seconds, when the atomized jet reaches a stage of being able to be injected from the handy probe, the handy probe is positioned into the oral cavity to direct the atomized jet injected from the tip end of the nozzle at a position between the tooth surface and the tooth gum, i.e., the entrance to the periodontal pocket at which the cleaning device has been aimed.

The compressed air produced by the air pump is fed into the handy probe through the air-feed tube. The compressed air, which has entered into the handy probe, is guided to the injection nozzle through the compressed air guide passage. When the compressed air passes through the tapered nozzle tip end, the compressed air is accelerated so that the tip end part of the nozzle is brought into a reduced-pressure condition, When the tip end part is brought into the reduced-pressure condition, the liquid agent is sucked out, by a pressure difference, from the tip end part of the liquid agent guide passage existing at the center position of the injection port, whereby the liquid agent, which has come outside from the tip end part of the liquid agent guide passage, rides on the flowing current of the compressed air to be dispersed in an atomized state, and the liquid agent is blown out as the atomized jet.

The atomized jet is not always required to be directed accurately between the tooth surface and the tooth gum, i.e., the entrance into the periodontal pocket. The reason for this is that, since the atomized jet to be blown out of the handy probe is mainly constituted of air, with a small amount of water contained therein, the fluid viscosity of the atomized jet is low. Hence, even when the atomized jet hits the tooth surface, a part of the atomized jet has its direction turned by the tooth surface and penetrates into the space between the tooth surface and the tooth gum, i.e., the entrance into the periodontal pocket, where cleaning is desired.

The liquid agent, containing water or liquid chemicals therein, is stored in a liquid storage tank which is either incorporated into the cylindrical part of the handy probe, or disposed in the close vicinity of the cylindrical part. The liquid agent can be atomized and injected from the tip end of the nozzle, even with compressed air at a jet-out pressure of as low as 0.05 to 0.80 kg/cm$^2$ to be produced by the air pump.

The atomized jet, containing the compressed air as the principal constituent, penetrates into a space between the tooth surface and the tooth gum, i.e., the entrance to the periodontal pocket, to force-open the gingiva which tightly closes the entrance, thereby causing a large quantity of the compressed air to penetrate into the periodontal pocket to kill the pathogenic fungi of periodontal disease.

A small quantity of liquid content in the atomized jet, to be injected from the tip end of the nozzle, serves to moisten the interior of the periodontal pocket and the area surrounding the periodontal pocket to impart the lubricating property thereto. In particular, when the liquid content consists of the liquid chemicals, various medical effects are exhibited in combination, such as sterilization, quenching, and so forth. Since the jet-out quantity of the liquid is extremely small, i.e., in a range of from 1 to 10 cc/min., the cleaning treatment can be performed on the entire periodontal pocket within the oral cavity, even when a liquid storage tank of a small capacity is incorporated into the handy probe.

When the compressed air guide passage is branched out, and one of the thus branched-out compressed air guide passages is introduced into the inner space of the liquid storage tank, the liquid surface within the liquid storage tank is pressed by the compressed air, whereby the liquid agent becomes pushed out into the liquid agent guide passage. This push-out function of the liquid agent cooperates with the drafting function of the liquid agent due to the pressure-reduction in the neighborhood of the jet-out port to thereby support squirting of the liquid agent on the compressed air. Even if the air pump is at a low capability, and the pressure-reduction is not sufficient, the liquid agent can be pushed out into the guide passages by pressing the liquid surface. Hence, the injection function of the atomized jet can be stabilized much more by means of this device even with an extremely low injection pressure of the compressed air, i.e., in a range of from 0.05 to 0.80 kg/cm$^2$.

Further, there is an additional function and effect resulting from introduction of the compressed air into the liquid storage tank, i.e., prevention of a vacuum in the interior of the liquid storage tank. More specifically, when no compressed air is introduced into the tightly closed liquid storage tank, the interior of the tank becomes close to a vacuum condition, as the liquid agent is being sucked out, with the consequence that it becomes difficult to suck out the liquid agent. In order to prevent this, an opening may be formed to introduce air into an appropriate place in the liquid storage tank from the outside. However, this would create a new problem such that the liquid agent would leak out through this opening if the liquid storage tank were overturned.

By introduction of the compressed air into the liquid storage tank, there is no possibility of creating a vacuum in the tank interior, even if the liquid storage tank is of a perfectly hermetic type. Hence, there is no possibility that the liquid agent will become difficult to suck out. Also, since a perfectly hermetic liquid storage tank can be utilized, no leakage of liquid takes place, even if the liquid storage tank were overturned.

Moreover, if an effective area of the air jet-out part, minus the area of the terminal end of the liquid guide passage at the jet-out port, is in a range of from 0.5 mm$^2$ to 20 mm$^2$, the injection pressure of the compressed air becomes more stabilized in a predetermined range, whereby preferred generation of the atomized jet can be ensured.

An optimum range of the injection pressure of the atomized jet to be blown out of the jet-out port exists. If the wind pressure is in a range of from 1 to 10 g/π•(5 mm)$^2$ at a spot which is 5 mm away from the jet-out port along the axial direction of the injection nozzle, an agreeable feel can be obtained in use, and there is no apprehension of the inner wall of the delicate and sensitive periodontal pocket being injury. Also, the distance of separation, between the jet-out port of the nozzle and the part to be injected at the time of actual use of the nozzle, is approximately 5 mm or less. Since, however, there is no substantial variations in the pressure with respect to variations in the distance within a range of 5 mm, the above-mentioned value becomes an effective index for the atomized jet pressure.

Further, when a part of the liquid agent guide passage, which is to be positioned, at least, at the jet-out port of the handy probe, is constituted of a flexible tube, the tube hangs downwardly under its own weight so as to be in a state in which no compressed air is being blown out. However, when the compressed air current is passing around the tube, the width in the radial direction of the passageway for the compressed air, which has been formed around the tube, becomes equal over the entire circumference so as to render the pressure at each and every part around the tube to be at an equal pressure, with the consequence that the existing position of the tube becomes automatically rectified. Hence, the tube becomes constantly positioned at the open center position of its injection port. Further, by maintaining the posture of the flexible tube, which is present at the open center position of the jet-out port, ejection of the atomized jet with uniform particle size can be secured.

Furthermore, when the tip end position of the flexible tube is within a range of ±2 mm in the axial direction of the injection nozzle, with respect to the open end position of the jet-out port, the function of the flexible tube, to be constantly positioned at the open center position of the jet-out port (i.e., the automatic centering function), can be exhibited with more stability.

In case the air pump is a diaphragm type compressor, and the drive source of the diaphragm is a reciprocating vibratory body utilizing the repulsion-attraction function of electromagnets and permanent magnets, air is pressurized by the opening-and-closing of the diaphragm and the valve. Since the passageway of air is completely shut off from the drive mechanism, clean compressed air can be fed into the handy probe.

As the method for controlling the start-stop of the atomized jet injection from the handy probe, as well as controlling the rate of its injection, a direct control of a feed rate of the compressed air is adopted by providing means for regulating the flow-rate of either the compressed air at an intermediate part of the compressed air guide passage of the handy probe, or of the air-feed tube for supplying the compressed air from the air pump into the handy probe and then, operating the regulating means. With this direct control method, if and when the flow rate of the compressed air is restricted, the width of vibration of the diaphragm becomes small and also the width of vibration of the reciprocating vibratory body, as the drive source, becomes small. Since the reciprocating vibratory body utilizes the repulsion-attraction function of the electromagnets and the permanent magnets, the limit to the width of vibration of the reciprocating vibratory body does not accompany generation of the excess current due to overloading which is caused when the motor revolution is regulated mechanically. Rather, the limit to the width of the vibration of the reciprocating vibratory body has its significance such that the load becomes reduced, which is associated with decrease in the power consumption.

Further, in case a motor-revolution type drive source is employed, a phenomenon takes place such that the injection pressure increases abnormally, when the flow-rate or blow-out quantity of the compressed air is restricted, and it becomes possible that the inner wall of the periodontal pocket will be injured by the atomized jet having abnormally increased pressure. However, when use is made of the reciprocating vibratory body as the drive source, there is no possibility of the pressure of the atomized jet becoming abnormally high, even if the flow-rate or blow-out quantity of the compressed air is regulated. This means that, during the use of the cleaning device of the present invention, even if a situation takes place such that the blow-out quantity of air is regulated by, for example, the tip end of the nozzle coming into contact with the entrance of the periodontal pocket and its surrounding region or the tooth gum, there is no possibility of the pressure of the atomized jet becoming abnormally high. Hence, the cleaning device is safer for use, and there is less danger of the inner wall of the periodontal pocket being injured. In addition, there is no necessity for increasing the pressure-resistance of the air feed tube more than required.

Also, when the control of the blow-out quantity of the atomized jet from the handy probe is realized by providing means for exhausting a part of the compressed air outside the compressed air guide passage or outside the air-feed tube, at an intermediate part of the air-feed tube for supplying the compressed air from the air-pump to the handy probe, no variations occur in the vibration amplitude of the diaphragm. Hence, no remarkable changes appear in the power consumption.

Further, in case the nozzle part or the intra-nozzle liquid conduit pipe is made separable from the main body of the handy probe, there is no risk of infection of the pathogenic fungi from one person to another, in so far as the nozzle part or the intra-nozzle liquid conduit pipe used by another person is discarded and replaced with a new one, or with a nozzle part or intra-nozzle liquid conduit pipe of previously used by the same person, even if, during use of one and the same cleaning device, such nozzle or intra-nozzle liquid conduit pipe should come into contact within the oral cavity. This is important for prevention of an infection within a hospital, if the cleaning device is to be used in a hospital. Depending on necessity, it is also possible to change the mode of injection of the atomized jet, in correspondence with variations in the position to be injected within the mouth, which can be realized by exchanging the nozzle part with a nozzle part having different length and shape. Furthermore, by changing the inner diameter of the intra-nozzle liquid conduit pipe, the blow-out quantity of the liquid agent can be varied.

Moreover, for the sake of convenience in supplying the cleaning device to the users, the injection nozzle and the intra-nozzle liquid conduit pipe are integrally joined together beforehand, which makes it possible to carry out simultaneous exchange of the injection nozzle and the intra-nozzle liquid conduit pipe, with the consequence that the insertion work of the intra-nozzle liquid conduit pipe into the injection nozzle becomes unnecessary.

It is an object of the present invention to provide a periodontal pocket cleaning device, which includes a handy probe provided with an air-jet ejection mechanism, an air pump for producing compressed air, and an air-feeding tube for feeding the compressed air from the air pump to the handy probe, with an improvement wherein the handy probe comprises: an injection nozzle with an jet-out port being provided at the tip end thereof; a liquid storage tank for storing therein liquid agent therein, the liquid agent containing water or liquid chemicals; a liquid agent guide passage for guiding the liquid agent in the liquid storage tank to the substantially center position of the jet-out port via the injection nozzle; and a compressed air guide passage for guiding the compressed air to be fed outside to a position which surrounds the liquid agent guide passage at the jet-out port via the injection nozzle, wherein the jet-out pressure of the compressed air to be ejected from the nozzle of the handy nozzle is set in a range of from 0.05 to 0.80 kg/cm$^2$, the jet-out quantity of the compressed air is set in a range of 2 to 30 l/min., and the jet-out quantity of the liquid agent is set in a range of from 1 to 10 cc/min.

BRIEF DESCRIPTION OF THE DRAWING

The above mentioned object, other objects, advantages, and features of the present invention will become more readily apparent and understandable from consideration of the following detailed description thereof, especially when taken in conjunction with the accompanying drawings, wherein:

FIG. 7($b$) is an explanatory diagram of the air ejection port, as viewed from a front thereof;

FIG. 8 is a graphical representation showing the results of the organoleptic tests for the feeling of use of the cleaning device, in case the wind pressure at a spot 5 mm distant from the injection port is varied;

FIG. 14($b$) is an explanatory diagram of the jet-out port as viewed from a front thereof;

FIG. 23 is a side elevational view, partly in longitudinal cross-section, showing a structure of the third embodiment of the handy probe according to the present invention;

FIGS. 24($a$), 24($b$) and 24($c$) are each an explanatory diagram, in cross-section, showing a structure of the inlet air quantity regulating part in the third embodiment of the handy probe;

FIGS. 27($a$), 27($b$) and 27($c$) are each a cross-sectional view showing the inlet air quantity regulating mechanism according to the fourth embodiment of the present invention;

DETAILED DESCRIPTION OF THE INVENTION

Figure 1:
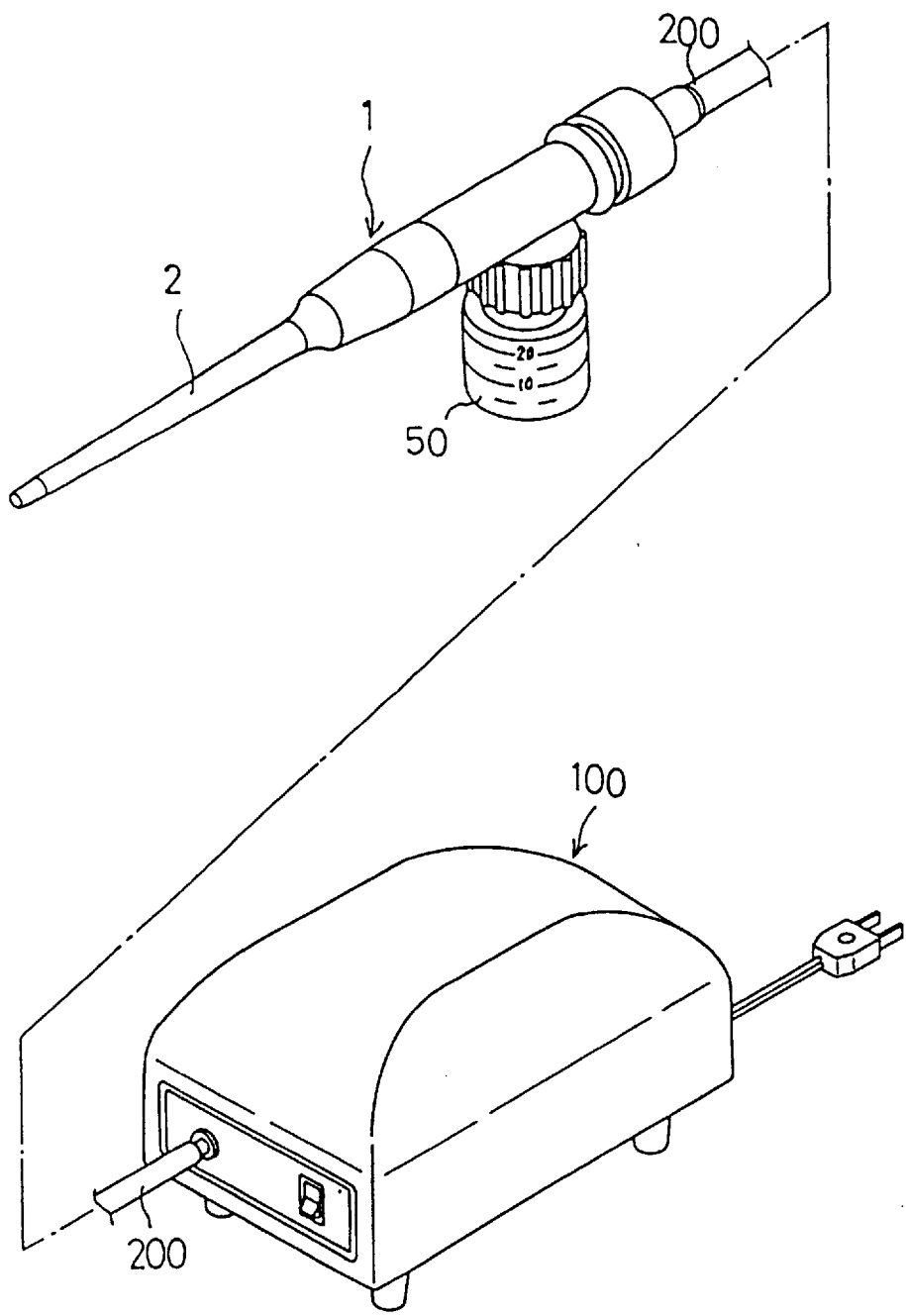
FIG. 1 is an explanatory diagram, in perspective view, showing the overall construction of the periodontal pocket cleaning device according to the present invention.

In the following, the present invention will be described in detail on the basis of the embodiments as shown in the drawing.

FIG. 1 is an explanatory diagram showing the general construction of the periodontal pocket cleaning device, according to the present invention. As shown in the drawing, the cleaning device, according to the present invention, is constructed with: a handy probe 1; an air pump 100 to produce compressed air; and an air-feeding tube 200 for supplying the compressed air produced by the air pump 100 into the handy probe 1.

The cleaning device, according to the present invention, is constructed so as to function in such a manner that the compressed air, produced by the air pump 100, is sent into the handy probe 1 through the air feeding tube 200 The compressed air, thus sent into the handy probe 1, is led into the injection nozzle 2 of the handy probe to be accelerated to render the tip end part of the injection nozzle in a state of reduced pressure. At the same time, a part of the compressed air in the handy probe 1 is introduced into the liquid storage tank 50 to push out the liquid agent in the liquid storage tank into the liquid agent guide passage. Both of these liquid suction and push-out functions are made to cooperate to draw up the liquid agent to the tip end position of the injection nozzle through the liquid agent guide passage. Then, the compressed air is blown out against the liquid agent, which has been drawn up at a high speed, to thereby spout the atomized jet from the tip end of the nozzle.

Figure 2:
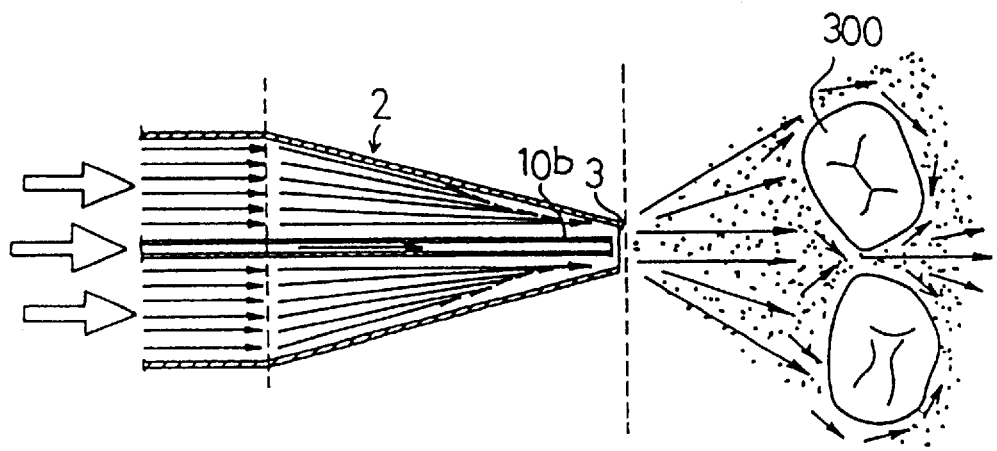
FIG. 2 is an explanatory diagram showing a mechanism, by which the atomized jet is generated at the tip end part of the nozzle, and a state of the thus generated atomized jet being sprayed on the tooth.

FIG. 2 illustrates a mechanism, by which the atomized jet is generated at the nozzle tip end and a state, in which the thus generated atomized jet, is blown against the tooth. An intra-nozzle liquid conduit pipe 10b is disposed on the axial position if the injection nozzle 2 to form the liquid agent guide passage to guide the liquid agent, such as water, liquid chemicals, etc., to the tip end of the nozzle. The compressed air passes through the surrounding area of the intra-nozzle liquid conduit pipe 10b, and is guided to the injection port 3. The injection nozzle 2 is tapered toward the tip end side thereof and because of this, the speed of the compressed air is accelerated as it reaches closer to the tip end of the injection nozzle 2. The speed of the compressed air is further accelerated to its maximum speed in the vicinity of the injection ( jet-out) port 3. The vicinity of the injection port 3 is brought to a state of reduced pressure by the passage of this accelerated air stream, so that the liquid agent in the liquid storage tank is drawn up by suction through the intra-nozzle liquid conduit pipe 10b, and continuously discharged through the open end of this intra-nozzle liquid conduit pipe. With the liquid agent having been discharged through the injection port 3, the compressed air, at its accelerated speed, comes into contact with the liquid agent to cause an impact force to be added to the liquid agent. The liquid gent is divided into small liquid particles by this impact force and is dispersed into the compressed air to become the atomized jet to be discharged through the jet-out port 3.

Figure 3:
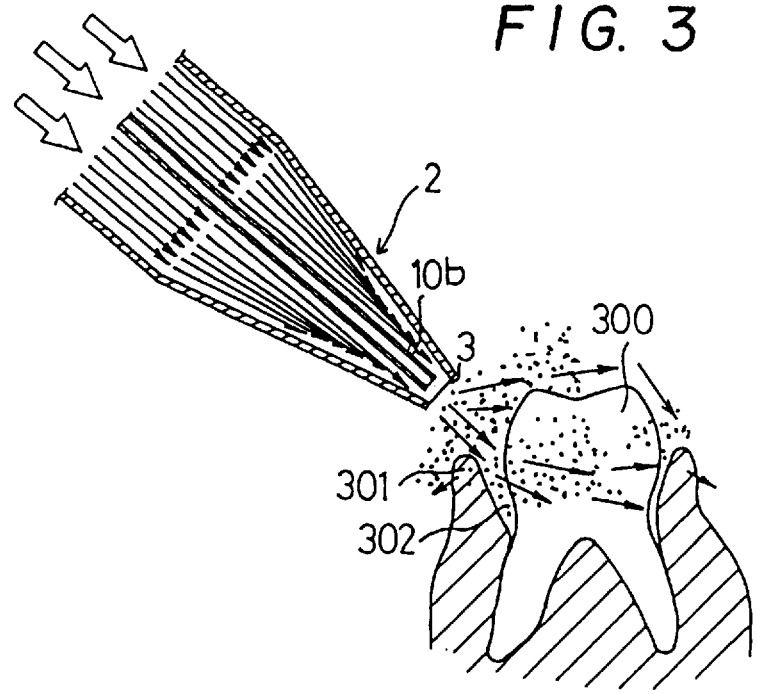
FIG. 3 is an explanatory diagram showing a mechanism, by which the atomized jet is generated at the tip and part of the nozzle, and a state of the thus generated atomized jet being sprayed on the tooth.

The atomized jet, which has been ejected from the injection port 3 and blown against the tooth 300, works to open the surface part of the tooth gum 301 under its wind pressure, as shown by arrows in FIG. 3. Thereafter, the atomized jet penetrates into the periodontal pocket 302 to expose the anaerobic bacteria in the interior of the pocket to the external air, thereby killing the anaerobic bacteria or suppressing its propagation. In the meantime, the atomized jet, which has not penetrated into the periodontal pocket of a tooth, comes around the tooth 300, and some of the atomized jet, which has come around the tooth, reaches the periodontal pocket of an adjacent tooth.

The atomized jet, to be ejected from the periodontal pocket cleaning device according to the present invention, contains a small quantity of water or liquid chemicals. Therefore, the atomized jet acts more like an "air jet" than a "water-current jet", and the fluid viscosity of the atomized jet, is much lower than the fluid viscosity of the water-current jet. Accordingly, even in the case of the atomized jet being unable to be blown against the entrance of the periodontal pocket as the target for cleaning, the atomized jet, which has hit the tooth surface, can still reach inside the periodontal pocket 302 by taking a detour course to the upper and lower sides, the left and right sides, and further the rear side of the tooth.

The atomized jet has various remarkable effects such that the liquid agent, such as water, liquid chemicals, etc., contained in the atomized jet, functions to impart moistness, by the blowing of the air jet, to the periodontal pocket 302, as well as the oral cavity, which is prone to become dry. More particularly, when the liquid agent consists of pharmaceutical preparations, such as disinfectant, quenching agent, dental plaque dissolving agent, dental caries preventive agent, preventive agent against dental calculus build-up, anastaltic agent, preventive agent against perception allergy, local anesthesia, anti-histamic agent, anti-biotic agent, or various others, there accrue, in addition to the disinfecting effect due to the air, various other effects proper to these pharmaceutical preparations, such as disinfecting effect, quenching effect, dental plaque dissolving effect, dental caries preventive effect, dental calculus build-up preventive effect, anastaltic effect, perception allergy preventive effect, anesthetic effect, and so forth.

In the following, each and every constituent part of the periodontal pocket cleaning device according to the present invention will be explained in detail.

First of all, explanations will be given as to the handy probe 1 to be used in the first embodiment of the present invention.

Figure 4:
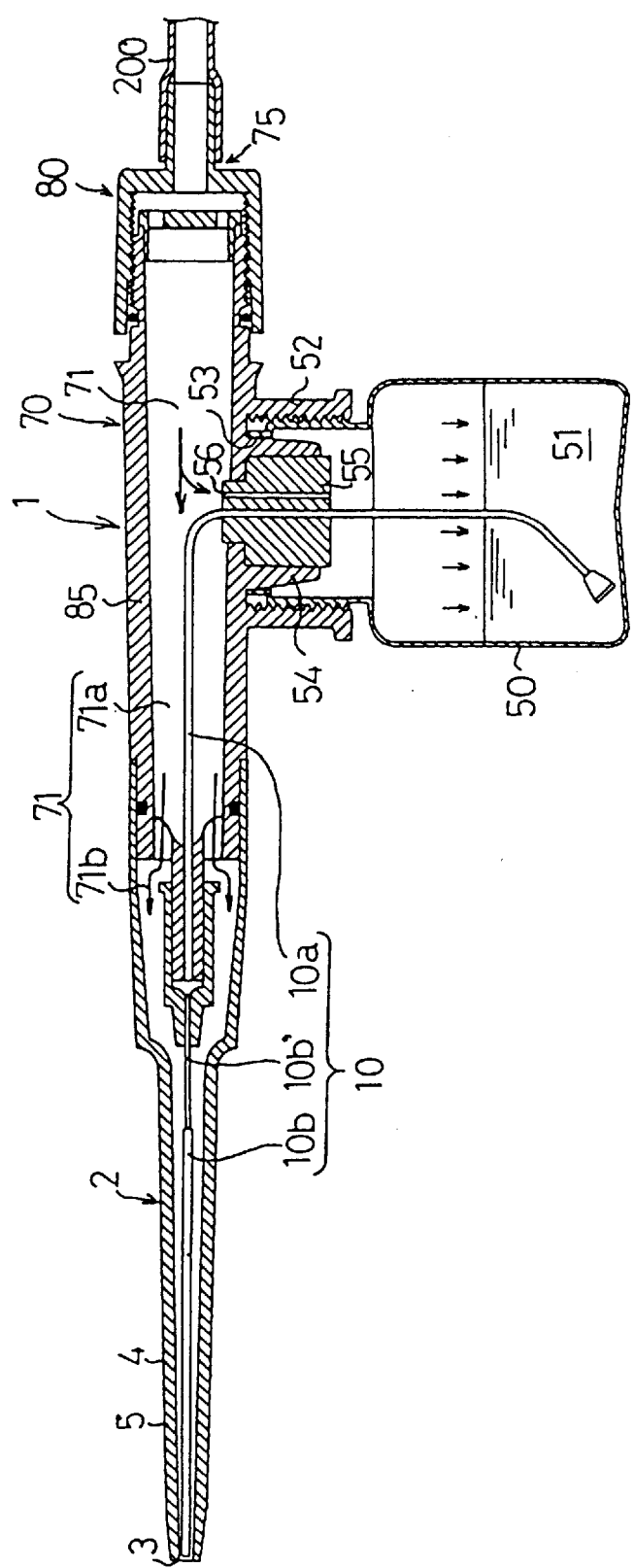
FIG. 4 is a side elevational view showing a structure of the first embodiment of the handy probe according to the present invention.

As shown in FIG. 4, the handy probe 1 is constructed with: the injection nozzle 2, the liquid storage tank 50 for storing liquid agent, such as water, liquid chemicals, etc., therein; and a cylindrical body 70. The liquid storage tank 50 is attached to the cylindrical body 70. Various mechanisms are incorporated into the cylindrical body 70 and the cylindrical body 70 also serves as the gripping pars of the handy probe 1.

In the interior of the handy probe 1, there are installed: the liquid agent guide passage 10 which connects the liquid storage tank 50 to the injection port 3 via the cylindrical body 70; and the compressed air guide passage 71 which serves as the guide path to lead the compressed air supplied from outside of the handy probe 1 to the injection port 3.

The liquid agent guide passage 10 constitutes the path for guiding the liquid agent 51 in the liquid storage tank 50 out of the liquid storage tank 50 and the path for introducing the liquid agent into the nozzle 2. This liquid agent guide passage 10 is constructed with: a liquid agent feeding tube 10*a* which constitutes the passageway from the liquid storage tank 50 to the injection nozzle 2; and intra-nozzle liquid conduit pipes 10*b*, 10*b*' which are connected to the liquid agent feeding tube 10*a*. On the other hand, the compressed air guide passage 71 is for leading the compressed air, supplied from the outside of the handy probe 1, into the injection port 3. The compressed air guide passage 71 is constructed with an extra-nozzle air-feeding path 71*a* formed within the cylindrical body 70, and an intra-nozzle air-feeding path 71*b* formed within the injection nozzle 2.

An atomized jet generating mechanism is constructed with the tip end part of the tapered injection nozzle 4 and the tip end part of the intra-nozzle liquid conduit pipe 10*b*.

Figure 5:
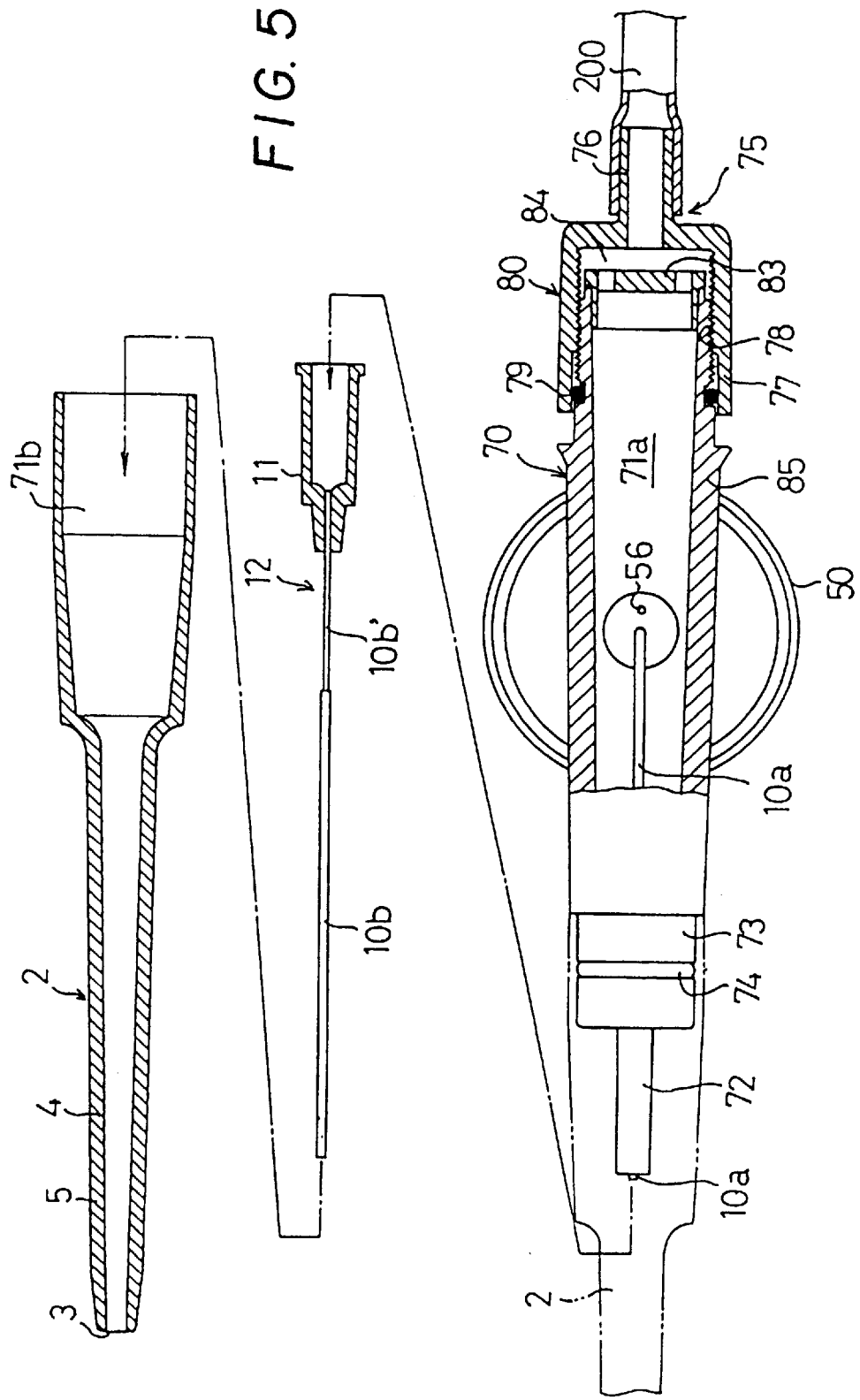
FIG. 5 is a plan view, partly in longitudinal cross-section, showing the handy probe in an exploded state.

FIG. 5 illustrates the handy probe 1 in detail, wherein the injection nozzle 2 and the intra-nozzle liquid agent feeding part 12 are shown to be separated from the cylindrical body 70.

The intra-nozzle liquid agent feeding part 12 is replaceable with respect to the cylindrical body 70. The construction of the intra-nozzle liquid agent feeding part 12 is such that the intra-nozzle liquid conduit pipe 10*b*, made of a flexible material having pliability and elasticity such as, for example, polyethylene, polyester, Teflon, vinyl chloride, silicone, and so forth, is connected to a cylindrical mounting part 11 with the intra-nozzle liquid conduit pipe 10*b*', made of a metal tube or a rigid synthetic resin tube, being interposed therebetween. The reason for not directly attaching the intra-nozzle liquid conduit pipe 10*b*, made of flexible tube, onto the cylindrical mounting part 11 is that exchange of the flexible tube is presupposed. It is, however, feasible that the intra-nozzle liquid conduit pipe 10*b*, which is made of a flexible tube, may be directly attached to the cylindrical mounting part 11.

By the way, it may be feasible to construct the intra-nozzle liquid conduit pipe 10*b*, as a whole, with any one of a needle-shaped metal tube, rigid synthetic resin tube, and similar. In this case, it becomes necessary to devise the tip end of the intra-nozzle liquid conduit pipe 10*b* in such a manner as to bring it to the center position of the injection port 3 (the details of which will be explained further below).

On the other hand, at the tip end (i.e., the left side as viewed on the drawing) of the cylindrical body 70, a connecting rod 72, to be joined with the intra-nozzle liquid agent feeding part 12, and a nozzle connecting part 73, to be joined with the injection nozzle 2, are protrusively provided. Further, the liquid feeding tube 10*a* is inserted into this connecting rod 72, with the tip end of the liquid feeding tube 10*a* being exposed from the connecting rod 72. Furthermore, an O-shaped ring 74 is fitted on and around the nozzle connecting part 73 so that the whole construction may be such that air-tightness can be maintained at the time of mounting the injection nozzle 2.

Fitting into the cylindrical body 70 of the nozzle connecting part 73 and the injection nozzle 2 is done in such a manner that, after the intra-nozzle liquid agent feeding part 12 is mounted on the connecting rod 72, the injection nozzle 2 is fitted on the nozzle connecting part 73. Incidentally, it is also possible to extend the liquid agent feeding tube 10*a*, as it is, without providing the connecting rod 72, and to cause this liquid agent feeding tube 10*a*, as extended, to undertake the function as the intra-nozzle liquid agent feeding part 12 as well as the intra-nozzle liquid conduit pipe 10*b*, although this is not shown in the drawing. The advantage to be derived from this construction, in this case, is that the number of constituent parts can be reduced. In this case, also, replacement of the injection nozzle alone is presupposed.

At the compressed air introducing part 75 to be provided at the base and side (i.e., the right side as viewed on the figure of the drawing) of the cylindrical body 70, a cylindrical connecting part 76 is provided, to which the air-feeding tube 200 is fastened, and an inlet air quantity regulating part 80 is provided, to limit the total quantity of the compressed air to be introduced into the cylindrical body 70 through the cylindrical connecting part 76.

Figure 6:
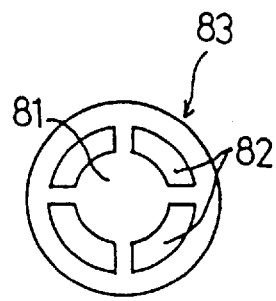
FIG. 6 is an explanatory diagram showing a structure of a plug to be used in an inlet air quantity regulating part.

This inlet air quantity regulating part 80 is of such a construction that, as shown in FIG. 6, a plug member 83, having a plurality of air passage holes 82, 82, ... formed around its shield plate 81, is fitted on the base end part of the cylindrical main body 85 constituting the cylindrical body 70, and a cap member 77, which is communicatively connected with the inner space of the cylindrical connecting part 76, is screw-connected, through a screw threaded part 78, with the base end part of the cylindrical main body 85, on which the plug member 83 is mounted. By rotating the cap member 77, a marginal space 84, between the plug member 83 and the cap member 77, is increased or decreased, thereby controlling the inlet quantity of the compressed air. Moreover, an O-ring 79 is interposed between the cylindrical main body 85 and the cap member 77 to maintain the air-tightness.

As shown in FIG. 4, the liquid storage tank 50 is constructed so that it may be integral with the cylindrical body 70 by screw-fitting the liquid storage tank 50 into a barrel-shaped cap 52, which is formed in one part of the cylindrical body 70 as an integral part thereof. An annular wall 54, protrusively formed from the cylindrical body 70, is fitted into an opening 53 of the liquid storage tank 50. A sealing plug 55, made of rubber, cork or similar, is fitted in the annular wall 54, through the sealing plug 55. The liquid agent feeding tube 10*a* is led out of the liquid storage tank 50.

A compressed air intake orifice 56 is formed in the sealing plug 55 so that a part of the compressed air, flowing through the compressed air guide passage 71 in the cylindrical body 70, may be branched out, as shown by arrow marks in the drawing, to permit the compressed air to be taken inside the liquid storage tank 50. Though not shown in the drawing, it can still further be envisioned that a small orifice is perforated directly in the lower wall of the cylindrical body 70, without use of the sealing plug. Through the small orifice, the liquid agent feeding tube 10*a* is led out and at the same time, the small orifice also functions as the compressed air intake orifice.

It is also devised that, by thus introducing the compressed air into the liquid storage tank 50 to press the liquid surface in the liquid storage tank 50, the liquid agent 51 becomes pushed out through the liquid agent feeding tube 10*a*. By making the liquid surface pressing function cooperate with the liquid agent intake function due to the pressure-reduction function at the tip end of the injection port 3, the generation of the atomized jet can be secured, even at a small injection pressure of the compressed air.

The small the diameter of the compressed air intake orifice 56 is, the better. The reason for this is that, if the diameter of the orifice 56 is too large, the liquid agent possibly flows outside, in a case where the handy probe 1 is overturned and the air pump 100 is not in operation. On the contrary, when the air pump 100 is in operation, the liquid surface is pressed by the compressed air as introduced into the liquid storage tank 50 through the compressed air intake orifice 56, on account of which, even when the handy probe 1 is handled in such a manner that it is turns upside down, no leakage of liquid takes place through the opening 53 and the compressed air intake orifice 56. Further, though not shown in the drawing, it may be feasible that a check valve, which is pushed open by the passage of the compressed air and is closed when the supply of the compressed air is stopped, is provided at the open end of the compressed air intake orifice 56 into the liquid storage tank 50. In such a case, no leakage of the liquid occurs, even when the supply of the compressed air is stopped.

The capacity of the liquid storage tank 50 should be sufficient, if it can contain a liquid agent of about 50 cc or so. Since the periodontic pocket cleaning device, according to the present invention, has a very small jet-out quantity of liquid agent, i.e., as small as 1 to 10 cc/min., the cleaning of all the periodontal pockets in the oral cavity can be done with about 50 cc's the liquid agent, without refilling the liquid agent. In addition, in view of the fact that the jet-out quantity of the liquid agent is small, there is no necessity for the liquid agent to be disgorged from the mouth over and over again during the pocket cleaning operation. Hence, the place for use of the cleaning device is not limited to the wash stand alone.

The liquid agent to be used is either water or liquid chemicals. The liquid chemicals to be used may be chosen from pharmaceutical preparations, such as disinfectant, quenching agent, dental plaque dissolving agent, dental caries preventive agent, dental calculus build-up preventive agent, anastaltic agent, perception allergy preventive agent, local anesthesia, anti-histamic agent, or anti-biotic agent.

As the disinfectant, chorohexydine, iodoglycerine, benzalkonium chloride, cetyl pyridinium, chlorohexydine gluconate, and others, may be used.

As the quenching agent, steroid type quenching agent, such as hydrocortisone, dexamethasone, and so forth; non-steroid type quenching agent, such as ibuprofen, indomethacin, and so on; and various other quenching agents, such as azulene, azulene sulfonate, β-glycyl recinoic acid, soft extract of ligusticum (root), sodium chloride, acetic acid d1-α-tocopherol, ε-aminocaproic acid, and so on, may be used.

As the dental plaque dissolving agent, lysozyme chloride, and others, may be used.

As the dental caries preventive agent, sodium monofluorophosphate, sodium fluoride, stannous fluoride, and so forth, may be used.

As the dental calculus build-up preventive agent, pyrophosphoric acid, zinc citrate, zinc chloride, AHP, and gantlettes acid, and so forth, may be used.

As the anastaltic agent, tranequisum acid, and so forth, may be used.

As the perception allergy preventive agent, aluminum lactate, potassium nitrate, potassium oxlate, strontium chloride, and so forth, may be used.

As the local anesthesia, procaine, lidocaine, and others, may be used.

Examples of the anti-histamic agent may be diphenehydramine chloride, chlorophenylamine maleinate, and so on.

Examples of the anti-biotic agent may be ampiciline, aminocycline chloride, tetracycline chloride, benzyl penicilline, and so forth.

By the way, the periodontal pocket cleaning device, according to the present invention, sets: the jet-out pressure of the compressed air ejected from the injection nozzle 2 to be in a range of from 0.05 to 0.80 kg/cm$^2$; the jet-out quantity of the compressed air to be in a range of from 2 to 30 l/min.; and the jet-out quantity of the liquid agent to be in a range from 1 to 10 cc/min. These numerical ranges have been derived from the fact that the periodontal pocket cleaning device, according to the resent invention, has its principal purpose of disinfection of the periodontal pathogenic fungi by air feeding, from the fact that the liquid agent is used to prevent the oral cavity from drying, to enforce the disinfection by the addition of the liquid chemicals, to attain the quenching effect, and so forth; and from the fact that the wash-out of the dental plaque and periodontal pathogenic fungi with use of the liquid agent is not taken into consideration.

The reason for setting the jet-out quantity of the liquid agent in a range of from 1 to 10 cc/min. is that the use of the liquid agent according to the present invention has two meanings, as mentioned above. First, preventing the oral cavity from being dried up and second, of exhibiting the enforced disinfection function and the quenching function, and so forth, or which purpose the quantity is set slightly less. This numerical range for the quantity is established on the criteria that the liquid agent needs not be spewed out so frequently for the disinfecting treatment of the entire periodontal pocket in one oral cavity, and yet splashes of the liquid agent will not be scattered here and there outside the periodontal pocket, and moreover, with further expectation such that sufficient medicinal efficacy can be obtained when the liquid chemicals are added to the liquid agent, or the oral cavity can be prevented from drying up. When the jet-out quantity of the liquid agent exceeds 10 cc/min., it tends to overflow from the mouth with the consequence that the liquid agent needs to be spewn frequently. On the other hand, when the jet-out quantity of the liquid agent is below 1 cc/min., it becomes unable to prevent the oral cavity from being dried up or to exhibit the medicinal efficacy resulting from use of the liquid chemicals. Hence, it has been concluded that the jet-out quantity of the liquid agent should be set in a range of from 1 to 10 cc/min., or more preferably from 2 to 7.5 cc/min.

In contrast to the jet-out quantity of the liquid agent being small according to the present invention, the jet-out quantity of the compressed air is set at a larger amount of from 2 to 30 l/min. This is because the periodontal pocket cleaning device, according to the present invention, has its principal purpose, the disinfection of pathogenic fungi with air. When the jet-out quantity of the compressed air is below 2 l/min., sufficient effect of disinfection cannot be exhibited. On the other hand, when its jet-out quantity exceeds 30 l/min., no improvement is seen in the disinfection effect commensurate with the increase in the jet-out quantity. Further, the increase in the jet-out quantity invites enlargement in the capacity of the air pump 100, so that it is not preferable to augment the jet-out quantity more than this set limit.

As important as the injection quantity of the compressed air is, the jet-out pressure of the compressed air is even more important. According to the present invention, the jet-out pressure of the compressed air is set at an extremely small value of from 0.05 to 0.80 kg/cm². A more preferred range of the jet-out pressure is from 0.20 to 0.80 kg/cm². The reason for this value setting is that the periodontal pocket cleaning device, according to the present invention, has a small quantity of the liquid agent to be sucked, and yet the liquid storage tank 50, in which the liquid agent is stored, is integrally combined with the cylindrical body 70 of the handy probe 1, or is disposed in proximity to the tank at a very short distance from the injection port 3, on account of which the suction of the liquid agent is possible, even if the state of the pressure-reduction in the vicinity of the injection port 3 is slight. When the jet-out pressure is high, there is an apprehension that the delicate and sensitive periodontal pocket could be injured. Further, with a high jet-out pressure, the air pump for the injection of the liquid agent must be made large in size with the consequent increase in the production cost of the device. From these points of view, the jet-out pressure of the compressed air is set at a value of 0.50 kg/cm² or below. On the other hand, the reason for setting the lower limit of the jet-out pressure of the compressed air to be 0.05 kg/cm² is that, when the jet-out pressure is below this value, the effect of opening the periodontal pocket is poor. A more preferred range of the jet-out pressure is from 0.10 to 0.30 kg/cm². By the way, when a part of the compressed air is branched out into liquid storage tank 50, as is the case with the above-mentioned embodiment, a highly stable atomized jet can be obtained, even if the pressure value is closer to the lower limit of the above-mentioned numerical range. Yet, the air pump 100, for its satisfactory use, may be small in size and low in cost.

Incidentally, important to determining the value of the jet-out pressure of the compressed air from the injection port 3, is a pressure to which the periodontal pocket is subjected in the actual use of the cleaning device. According to the research and study done by the present inventors, this pressure has been evaluated as the wind pressure, to which a circular disk of 5 mm in radius is subjected at a spot 5 mm distant from the injection port 3 along the axial direction of the injection nozzle 2, the pressure value of which has been found preferably to be set in a range of from 1 to 10 g, i.e., 1 to 10 g/π•(5 mm)². By a spot of 5 mm distant from the injection port 3, a distance is meant which corresponds to a length between the injection port 3 and the periodontal pocket, when the cleaning device is in actual use. If the pressure is below 1 g, the user feels shaky and helpless in its use. On the contrary, when the pressure value exceeds 10 g, the user feels pain around the pocket to be cleaned, and it is possible that the delicate and sensitive periodontal pocket could be injured. By the way, in the actual use of the cleaning device, the distance between the injection port 3 and the periodontal pocket becomes shorter than 5 mm. However, it has also been verified that, within 5 mm distance, the wind pressure makes substantially no difference and the wind pressure, to which the periodontal pocket is subjected, can be uniformly determined and evaluated based on the above-mentioned criteria.

FIG. 8 shows the results of the organoleptic tests which have been conducted in deriving the above-mentioned wind pressure range of 1 to 10 g/π•(5 mm)². The test was done by laterally injecting the compresses air against the tooth surface at a part corresponding to the gingival margin with a width of 2 to 3 cm, whereby stimulus felt at the gingiva due to the pressure was evaluated in six stages of from zero (0) to five (5). Ten (10) testees were employed, and the particulars of each of the evaluation stages (0 to 5) are as follows.

0 . . . almost no pressure felt
1 . . . stimulus felt, but unsatisfactory
2 . . . appropriate stimulus felt
3 . . . forceful stimulus felt, but tolerable
4 . . . pain felt
5 . . . unbearable pain felt, unsuitable for use It has been discovered that, as shown in FIG. 8, appropriate stimulus, excellent in feel during use, could be obtained at a wind pressure range of from 1 to 10 g/π(5 mm)².

Figure 7A:
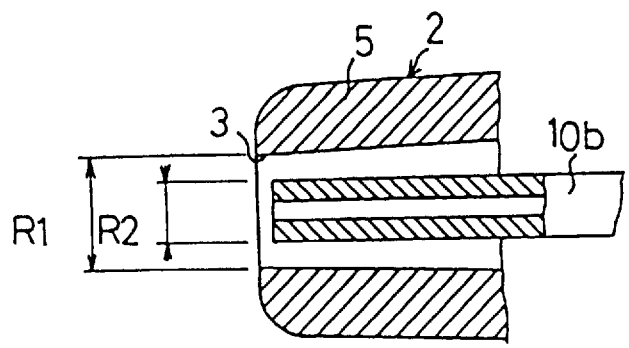
FIG. 7($a$) is an explanatory diagram, in longitudinal cross-sectional view, showing the effective area of an air jet-out part at the air ejection port.
Figure 7B:
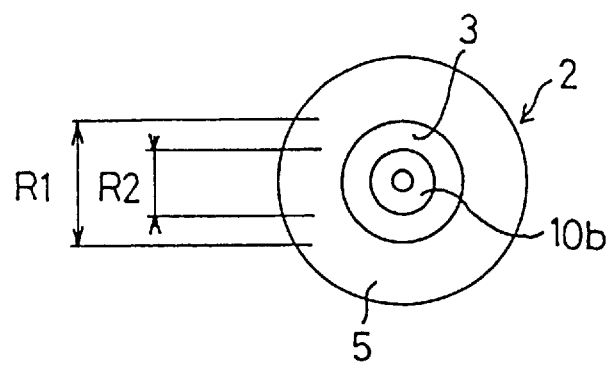

The factors to define such wind pressure range are the jet-out pressure of the compressed air as well as the effective area of the air jet-out part in the injection port 3. The effective area of the air jet-out part is the area of the injection nozzle 3, from which the intra-nozzle liquid conduit pipe 10b is removed, as illustrated in FIGS. 7(*a*) and 7(*b*), which can be expressed by the use of the sizes as shown in the figure of the drawing, as follows: π•(R1²–R2²).

The present inventors have conducted experiments to determine the effective area of the air jet-out part where this surface pressure is obtained, in accordance with the following method.

Figure 9:
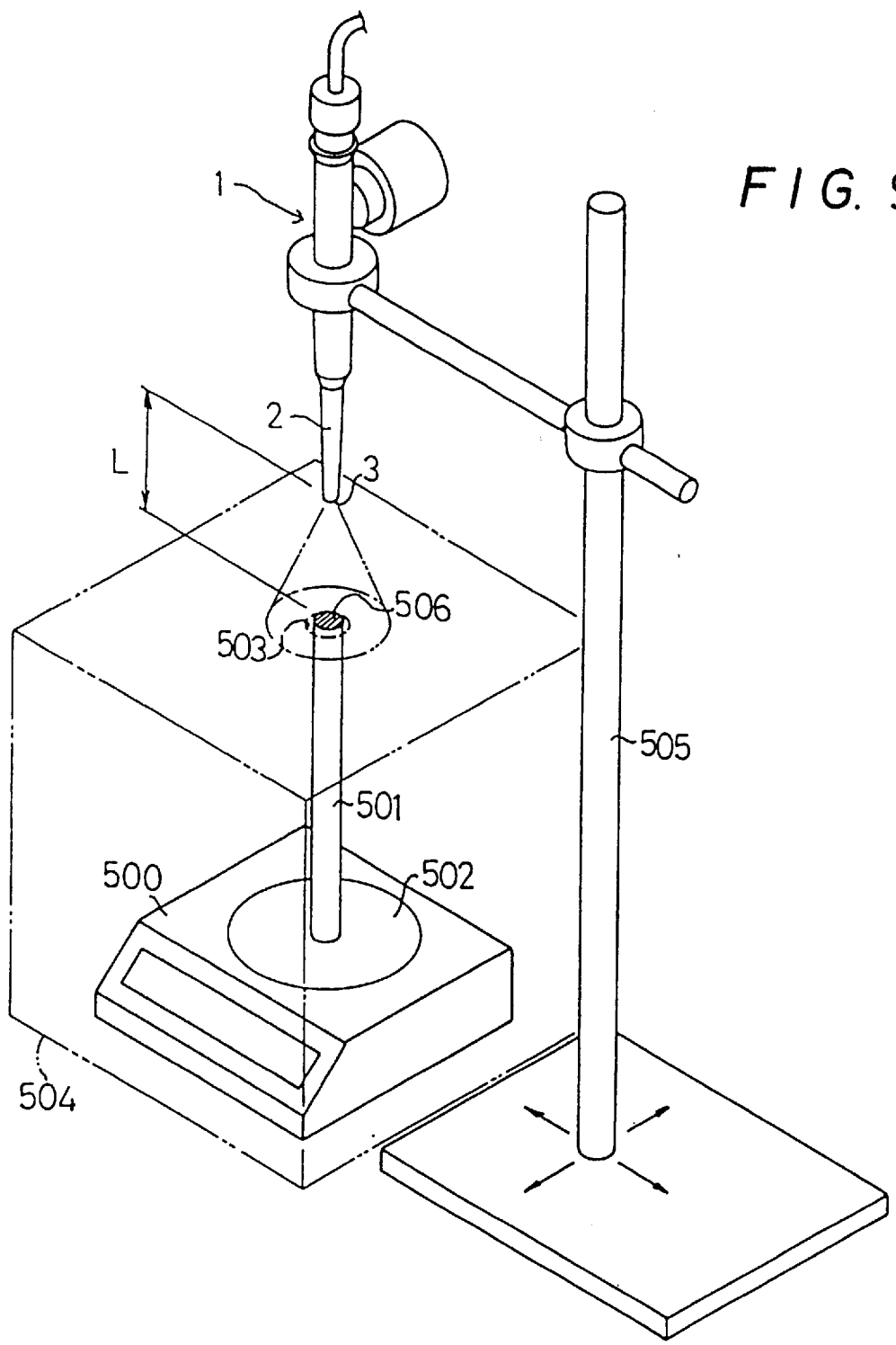
FIG. 9 is an explanatory diagram showing an experimental apparatus for finding the effective area of the air jet-out part at the injection port.
Figure 10:
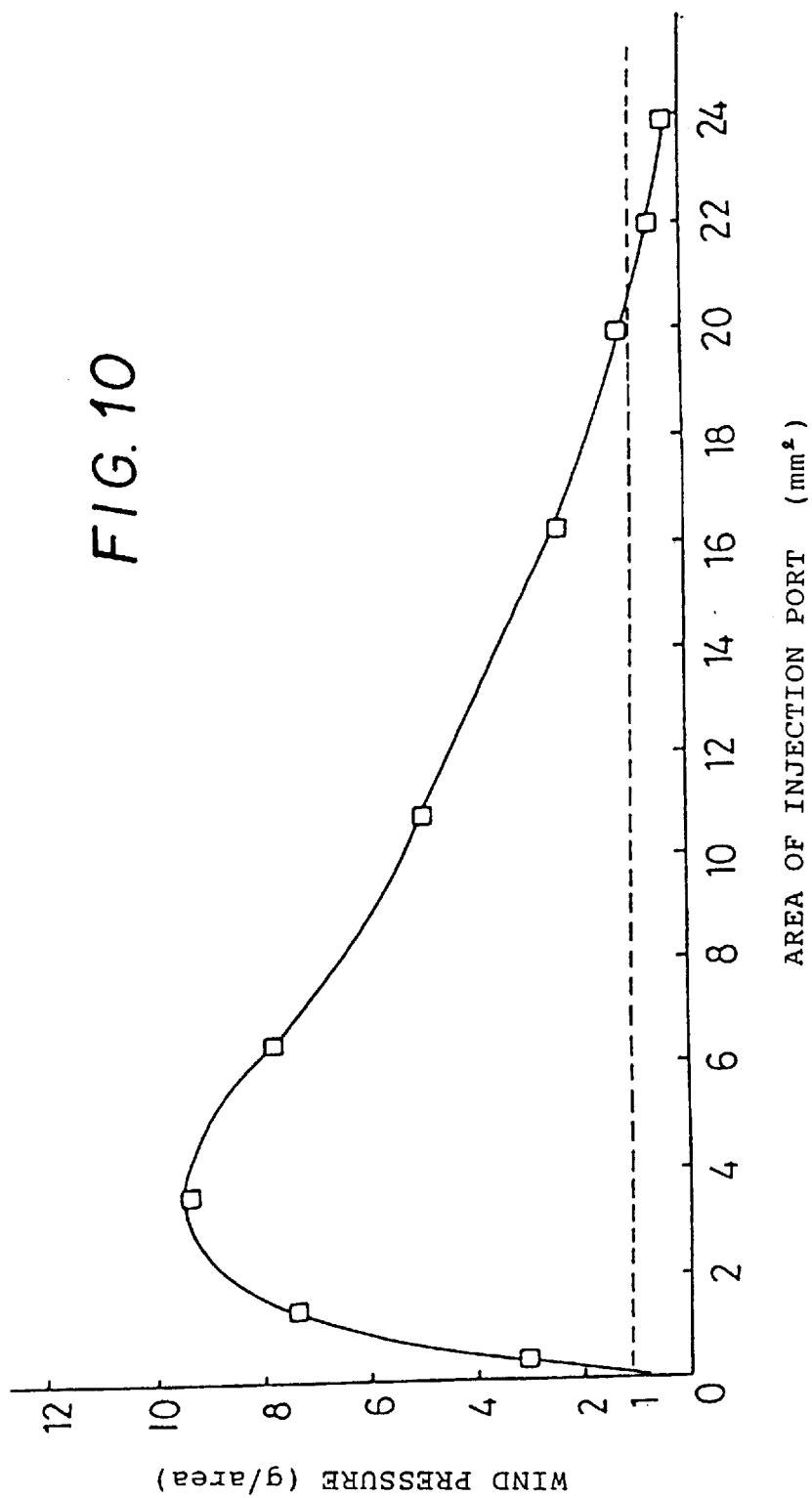
FIG. 10 is a graphical representation showing a relationship between the wind pressure and the effective area of the air jet-out part, as measured by the experimental apparatus shown in FIG. 9.

As shown in FIG. 9, a measuring apparatus was constructed by: erecting, on an electronic balance 500, a rod 501 having a tip end area ofπ•(5 mm)² and having a base part being supported by a supporting table 502; then, enclosing the rod 501 and the electronic balance 500 by a box 504 with a hole 503 of 12 mm in diameter having been perforated on its top surface; thereafter, causing the rod 501 to pass through the hole 503 while not contacting with the hole 503, and while exposing the top end surface 506 of the rod 501 to the outside of the box 504; on the other hand, supporting the injection nozzle 2 of the handy probe 1 by a stand 505 so that the axis of the injection nozzle 2 is in alignment with the axis of the rod 501. Using this measuring apparatus, a distance L, between the top end surface 506 of the rod 501 and the injection port 3, was set at 5 mm. While changing the inner diameter R1 of the nozzle outer cylinder 5, measurement was done for the jet-out pressure, to which the top end surface 506 of the rod 501, supposed to constitute the surface within the oral cavity where the compressed air is injected, is subjected, and the measured results were recorded. The results of the measurement are shown in FIG. 10. It was verified that, as shown in this graphical representation, if the effective area of the air jet-out part is in a range of from 0.5 mm² to 20 mm², the surface pressure which the top end surface 506 is subjected to could be in the range of 1 to 10 g. From this, it was concluded that the effective area of the air jet-out part in the injection port 3 should be set in the range of from 0.5 mm² to 20 mm². Incidentally, this effective area of 20 mm² substantially corresponds to the area of the circular disc having 5 mm in diameter.

In the next place, it was verified by experiments as to what relationship exists between the magnitude of the wind pressure which the top end surface 506 undergoes at the spot 5 mm distant from the injection nozzle 2 along its axial direction and the reaching distance of the atomized jet to the innermost part of the periodontal pocket.

This experiment was carried out by preparing a pseudo-model, which is supposed to be the periodontal pocket, with use of agar, in which is mixed resazurin, a reagent which changes its color upon its contact with oxygen, then injecting the atomized jet from the handy probe toward the surface of the agar to be penetrated into the interior of the agar to observe the change in the color tone of the agar. The agar was prepared in a substantially equal degree of hardness as that of the gingiva, and the experiments were conducted in the procedural sequences to be described further below.

The composition of the resazurin agar is as follows:

NaCl: 8.6 g KCl: 0.3 g

CaCl$_2$•2H$_2$O: 0.33 g Resazurin•Na Salt

Cystein•Hcl: 0.5 g: 0.01 g

Distilled water Agar: 20.0 g (as a whole): 1.01 1/5NaC: approx. 20 ml.

Figure 11:
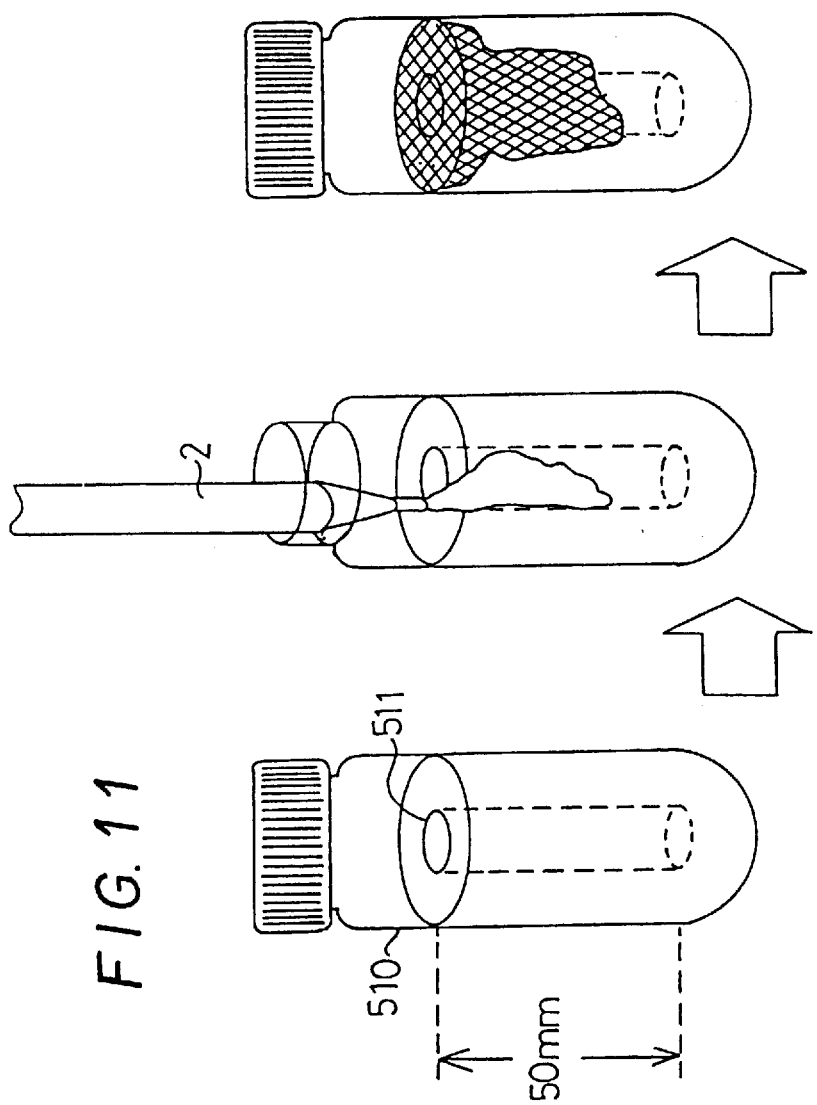
FIG. 11 is an explanatory diagram showing the experimental method for an oxygen reaching test with use of resazurin agar.

Each of the above-mentioned components was mixed under heat, and the composition was poured into a transparent vessel 510 with a closure cap having 50 ml capacity, as shown in FIG. 11. Subsequently, the container was cooled down, and then oxygen within the vessel 510 was purged from the anaerobic box (after drawing a vacuum, a mixed gas other than oxygen is sealed into the vessel 510). Thereafter, a plastic pipe of 1 cm in diameter with a thin wall thickness was thrust into the agar from its surface to thereby form a circular incision 511 therein at a depth of 5 cm.

The thus prepared test specimen (i.e., the vessel 510 containing the resazurin agar therein) was taken out of the anaerobic box, and the closure cap was opened. Then, the injection nozzle 2 of the handy probe 1 was promptly positioned in the vessel 510, and the compressed air was injected for three seconds aiming at the incision 511 from a position 5 mm above the incision 511.

Thereafter, the closure cap was tightened, and after lapse of certain definite hours, the change in the specimen was photographed. From the developed photograph, evaluation was made as to the color tone of the discolored region as well as the depth of the discolored region. The evaluation was done for ten (10) specimens, each in three levels.

0 . . . colorless or very pale red with indistinct contour

1 . . . pale red

2 . . . distinct red

Figure 12:
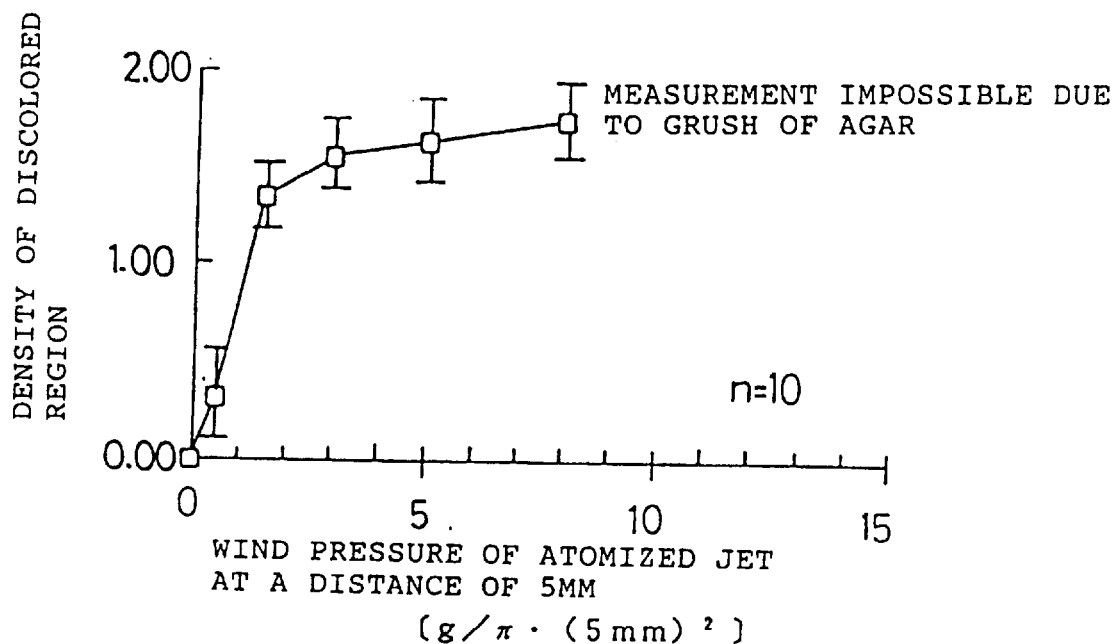
FIG. 12 is a graphical representation showing the results of the oxygen reaching test.
Figure 13:
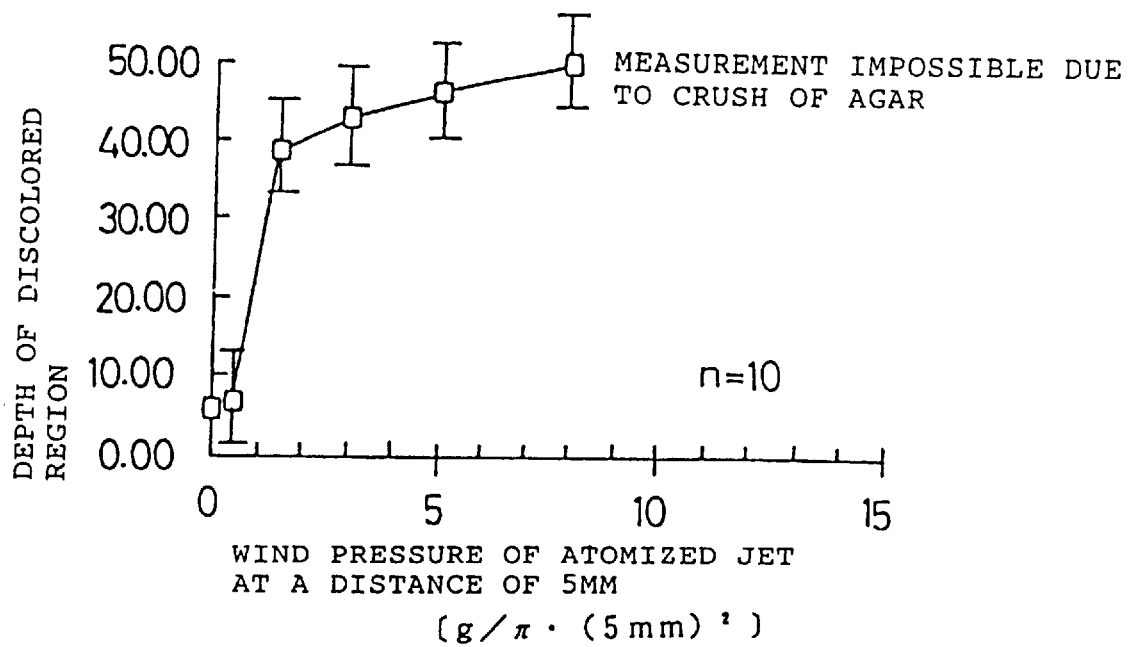
FIG. 13 is also a graphical representation showing the results of the oxygen reaching test.

The test results are shown in FIGS. 12 and 13. From these results, it was verified that, with the wind pressure of 1 g/π•(5 mm)$^2$ and higher to hit upon the specimen at a spot which is 5 mm distant from the injection nozzle 2 along its axial direction, oxygen could be made to reach a sufficiently deep position. At the same time, it was confirmed that, even when the wind pressure was increased higher than necessary, the depth of penetration of oxygen could not become so deep.

Also, the present inventors conducted clinical tests on those patients suffering from marginal periodontitis. In this case, it was also verified that, when the habit of using the periodontal pocket cleaning device, according to the present invention, continued three times a day (i.e., after breakfast and lunch, and before going to bed), an improvement was observed such that the depth of the periodontal pocket became shallow.

In the following, consideration is given to the positional relationship of the intra-nozzle liquid conduit pipe 10b at the jet-out port 3. In order to inject the stable atomized jet, it is necessary to position the intra-nozzle liquid conduit pipe 10b at the center of the jet-out port 3. If the tip end position of the intra-nozzle liquid conduit pipe 10b deviates from the center position of the nozzle outer cylinder 5, turbulence occurs in the flow of air passing through the intra-nozzle air feeding passage 71b which surrounds the intra-nozzle liquid conduit pipe 10b with the consequence that a difference is created in the state of the pressure-reduction around the intra-nozzle liquid conduit pipe 10b. This difference in the pressure reduction prevents the particle diameter of water drops contained in the jet current to be ejected from being uniformly and finely divided, thus resulting in the coarser particles of water drops. In addition, a phenomenon occurs such that the jet current pulsates and its direction of injection becomes unstable. Furthermore, in case the direction if the intra-nozzle liquid conduit pipe 10b deviates considerably so as to be in contact with the inner wall of the nozzle outer cylinder 5, as indicated by an imaginary line in the drawing, the liquid agent which has been drawn out of the intra-nozzle liquid conduit pipe 10b comes down along the inner wall of the nozzle outer cylinder 5, and a part of it drips down, with the consequence that atomization of the liquid agent cannot be done perfectly.

Figure 14A:
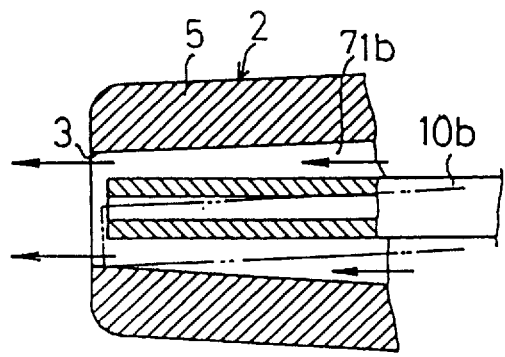
FIG. 14($a$) is an explanatory diagram, in longitudinal cross-sectional view, showing an influence on the atomized jet given by the positional relationship of the intra-nozzle liquid conduit pipe in the vicinity of the injection port.
Figure 14B:
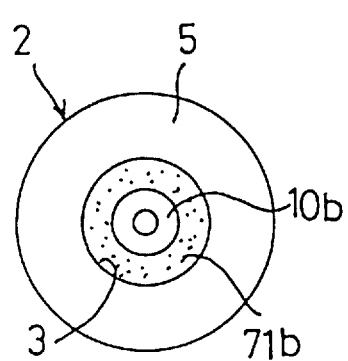

For the atomized jet, which contain uniformly divided, fine water drops therein, to be ejected stably, it is necessary that the intra-nozzle liquid conduit pipe 10 b be accurately positioned at the center of the jet-out. According to the embodiment shown in FIGS. 4 and 5, there has been proposed, as the method for attaining this purpose, to employ a flexible tube for the intra-nozzle liquid conduit pipe 10b. In case the flexible tube is used for the intra-nozzle liquid conduit pipe 10b, it remains in contact with the inner wall of the nozzle outer cylinder 5, under its own weight, when there is no ejection of the compressed air, as shown by an imaginary line in FIG. 14(a). However, when the compressed air is ejected, it exerts such force, to the intra-nozzle liquid conduit pipe 10b, that the clearance for its passage at each surrounding part of the flexible tube is equalized, thereby effecting "automatic centering" of the tip end of the intra-nozzle liquid conduit pipe 10b to bring it to the center position of the jet-out port 3. With use of this mechanism, the intra-nozzle liquid conduit pipe 10b becomes automatically positioned at the center of the jet-out port 3, when using the periodontal pocket cleaning device according to the present invention. As a consequence, high precision in the assembling work becomes unnecessary, which would contribute to reduction in the manufacturing cost of the cleaning device and at the same time, replacement of the injection nozzle 2 and the intra-nozzle liquid agent feeding part 12 becomes facilitated.

Further, with use of such flexible tube, the automatic centering can be done to bring the tube to the center position of the injection port 3, even if the nozzle outer cylinder 5 is non-rectilinear. Therefore, even when the tip end part of the nozzle outer cylinder 5 is curved, the intra-nozzle liquid conduit pipe 10b can be accurately and automatically brought to the center position of the injection port 3, which is the great advantage. In case the injection nozzle 2 is rectilinear throughout its length, when the atomized jet is to be directed to the periodontal pocket situated at the innermost part of the oral cavity, unnatural posture should unavoidably be taken. However, if the tip end of the nozzle is curved, there is no necessity for taking such unnatural posture. In case a needle-shaped metal tube or rigid synthetic resin tube is used for the intra-nozzle liquid conduit pipe 10b, it is extremely difficult to insert the intra-nozzle liquid conduit pipe 10b into the nozzle outer cylinder 5 with its tip end being curved.

Figure 15:
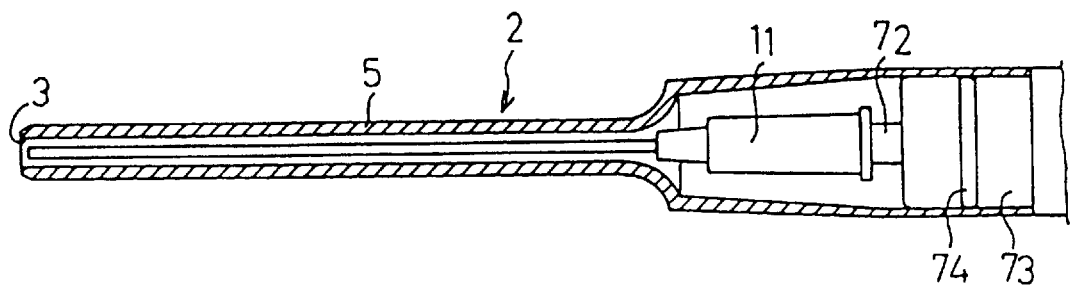
FIG. 15 is a longitudinal cross-sectional view showing another modified embodiment of the injection nozzle and the intra-nozzle liquid conduit pipe.
Figure 16:
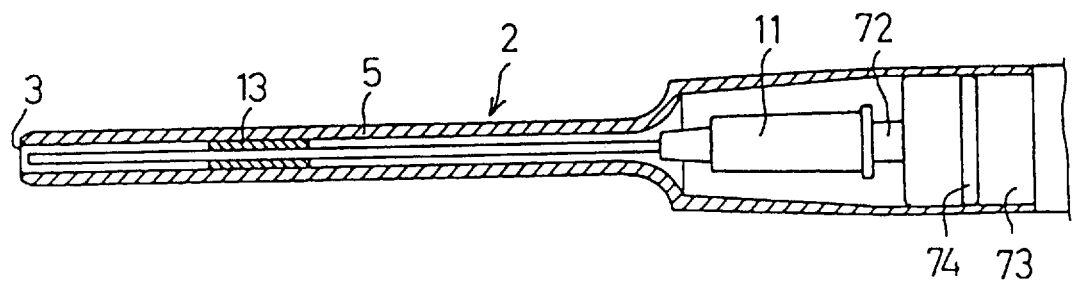
FIG. 16 is also a longitudinal cross-sectional view showing still another modified embodiment of the injection nozzle and the intra-nozzle liquid conduit pipe.

Even if the injection nozzle is rectilinear in shape, it is very difficult to accurately position the needle-shaped metal tube or the rigid synthetic resin tube at the center of the injection port 3. FIG. 15 illustrates a case, wherein the intra-nozzle liquid conduit pipe 10b, such as needle-shaped metal tube or the rigid synthetic resin tube, is inserted into the rectilinear injection nozzle 2. As seen from the drawing, for the tip end part of the intra-nozzle liquid conduit pipe 10b to be accurately positioned at the center of the injection port 3, fitting precision between the connecting rod 72 and the cylindrical mounting part 11, as well as the fitting precision between a nozzle-connecting part 73 and the injection nozzle 2, needs to be highly accurate. However, it is not at all easy to secure precision in such an assembly. As an expedient for solving this problem, it is considered that a spacer 13, of a structure which does not hinder passage of the compressed air, is interposed, as shown in FIG. 16, between the nozzle outer cylinder 5 and the intra-nozzle liquid conduit pipe 10b.

Figure 17:
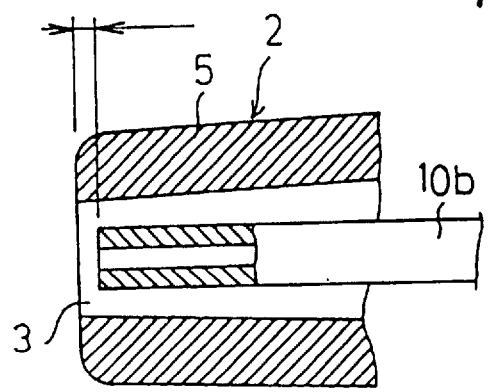
FIG. 17 is an explanatory diagram for explaining the influence given on the atomized jet by the positional relationship in the axial direction of the intra-nozzle liquid conduit pipe in the vicinity of the jet-out port.
Figure 18:
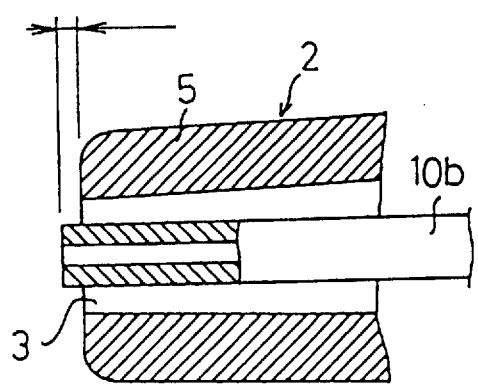
FIG. 18 is an explanatory diagram for explaining the influence given on the atomized jet by the positional relationship in the axial direction of the intra-nozzle liquid conduit pipe in the vicinity of the jet-out port.

In the following, consideration is given to the tip end position of the flexible tube, when such flexible tube is used for the intra-nozzle liquid conduit pipe 10b. As shown in FIG. 18, there is no obstacle to the automatic centering function, if the flexible tube is protruded slightly from the injection port 3. However, when its length becomes longer than a certain definite length, such automatic centering function no longer works, and there is an apprehension that the dental plaque will adhere to the tip end of the flexible tube during use of the cleaning device. Moreover, as shown in FIG. 17, in a case where the tip end of the intra-nozzle liquid conduit pipe 10b is set back from the injection port 3, if the set-back quantity is too large, there would take place a phenomenon such that, even if the compressed air is fed, the intra-nozzle liquid conduit pipe 10b comes into contact with the inner wall of the nozzle outer cylinder 5, or the liquid chemicals, ejected as the atomized jet, collide against the inner wall of the nozzle to be transformed again into coarse water drops. From these phenomena, it has been verified that the position of the tip end part of the flexible tube should preferably be in a range of ±2 mm in the axial direction of the nozzle, with respect to the injection port 3.

Figure 19:
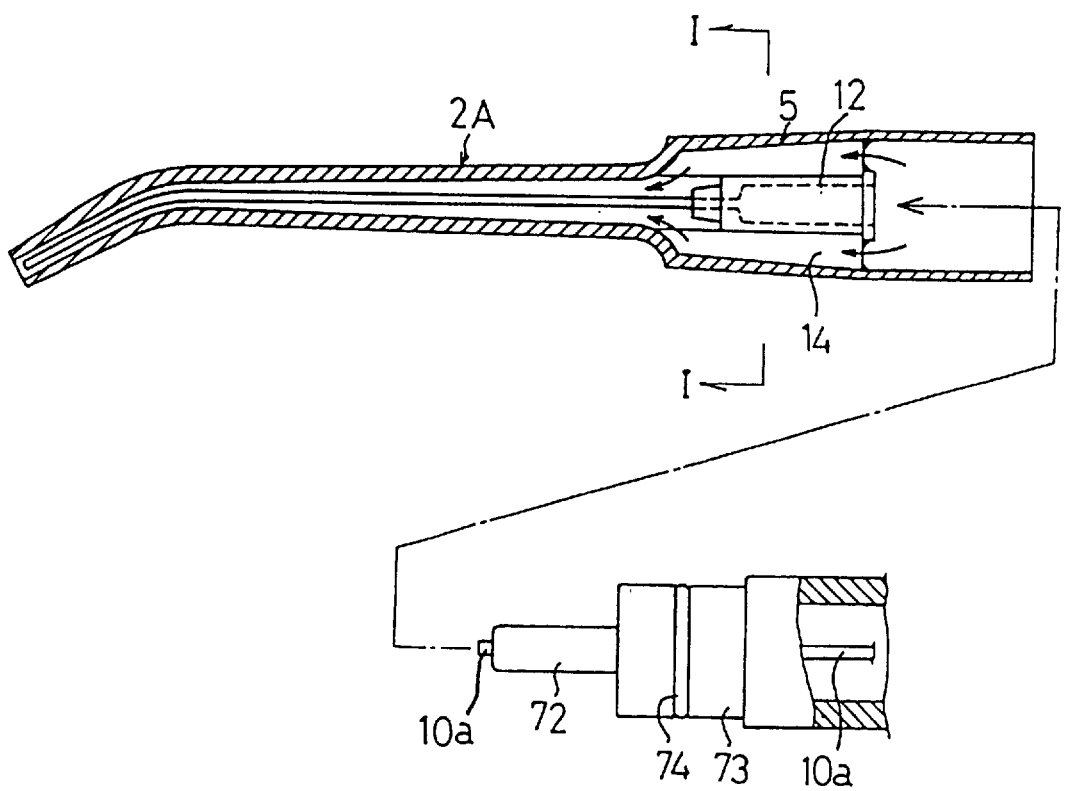
FIG. 19 is a longitudinal cross-sectional view showing another modified embodiment of the injection nozzle and the intra-nozzle liquid conduit pipe.
Figure 20:
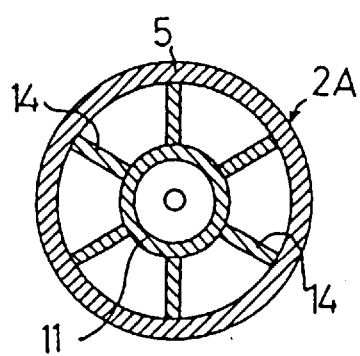
FIG. 20 is an enlarged cross-sectional view, taken along the line I—I in FIG. 15.

FIG. 19 illustrates a case, wherein the intra-nozzle liquid agent feeding part 12 is incorporated in the injection nozzle 2A with its tip end being curved. As shown in FIG. 20, the intra-nozzle liquid agent feeding part 12 is held within the nozzle by means of a plurality of legs 14, 14, . . . disposed radially as shown in FIG. 20. Thus, in the case of adopting a mode of embodiment, wherein the injection nozzle 2A and the intra-nozzle liquid agent feeding part 12 are integrally associated in advance to be offered to users, such users who purchase the product will become free from taking trouble in exchanging the intra-nozzle liquid agent feeding part 12 and the injection nozzle 2A. Accordingly, when the handy probe 1 is used conjointly among a plurality of persons, the exchange of the injection nozzle 2A and the intra-nozzle liquid agent feeding part 12 can be done quickly at the time of changing of the users. Moreover, since the cleaning device can be delivered to the users in the state of the intra-nozzle liquid agent feeding part 12 being assembled beforehand, with the injection nozzle 2A at high precision, by the manufacturer, for the ready use by the users, poor generation of the atomized jet caused by inadequate assembling, which tends to occur when such intra-nozzle liquid agent feeding part 12 and the injection nozzle 2A are put together by the user himself/herself, can be avoided.

Figure 21:
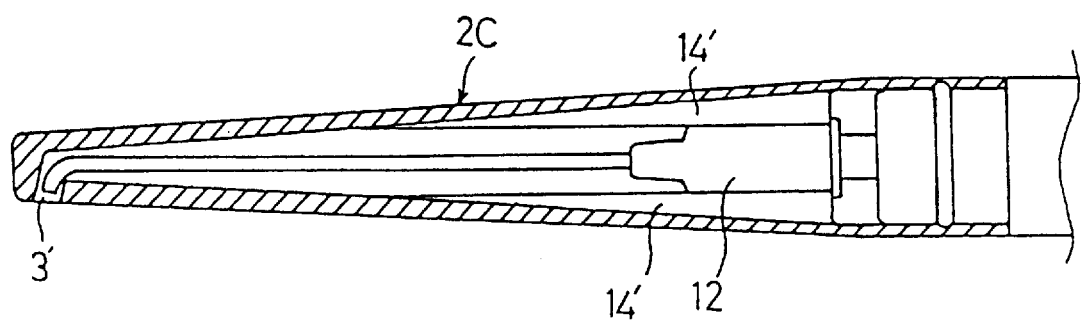
FIG. 21 is a longitudinal cross-sectional view showing another modified embodiment of the injection nozzle and the intra-nozzle liquid conduit pipe.

FIG. 21 is a modified embodiment of the injection nozzle. In this embodiment, the external shape of the injection nozzle 2C is rectilinear, and the tip end part of the intra-nozzle liquid agent feeding part 12 is bent within the body of the injection nozzle 2C, so as to appear at a jet-out port 3' for the nozzle formed at one peripheral part of injection nozzle 2C. In this case, the handy probe 1 can be operated, with a sense of handling the same, as if the user would handle an ordinary tooth brush. Hence, the user can easily direct the jet-out port 3' to the cheek side or tongue side within the oral cavity. This injection nozzle 2C also has an advantage such that, in comparison with that as shown in FIG. 19, it is more refined from the standpoint of its design.

Figure 22:
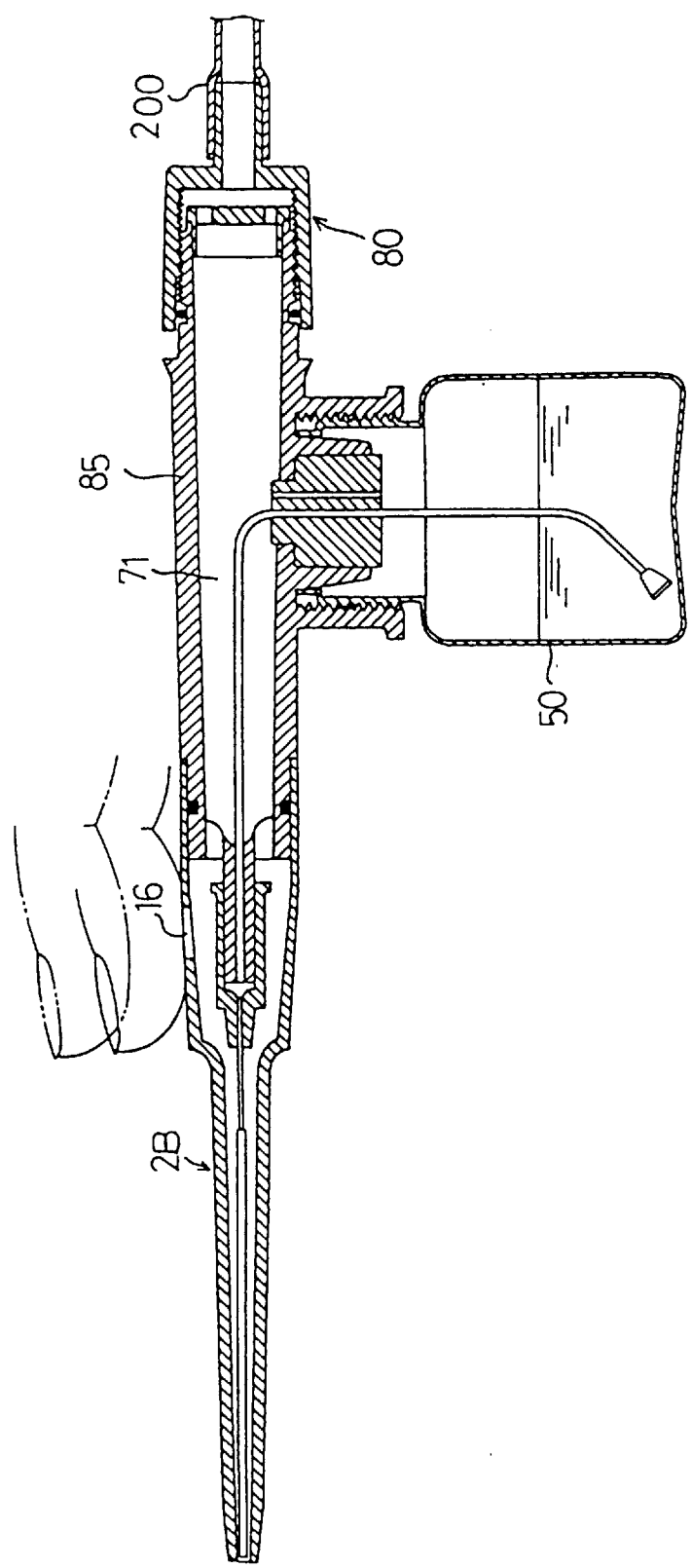
FIG. 22 is a side elevational view, in longitudinal cross-section, showing a structure of the second embodiment of the handy probe according to the present invention.
Figure 25:
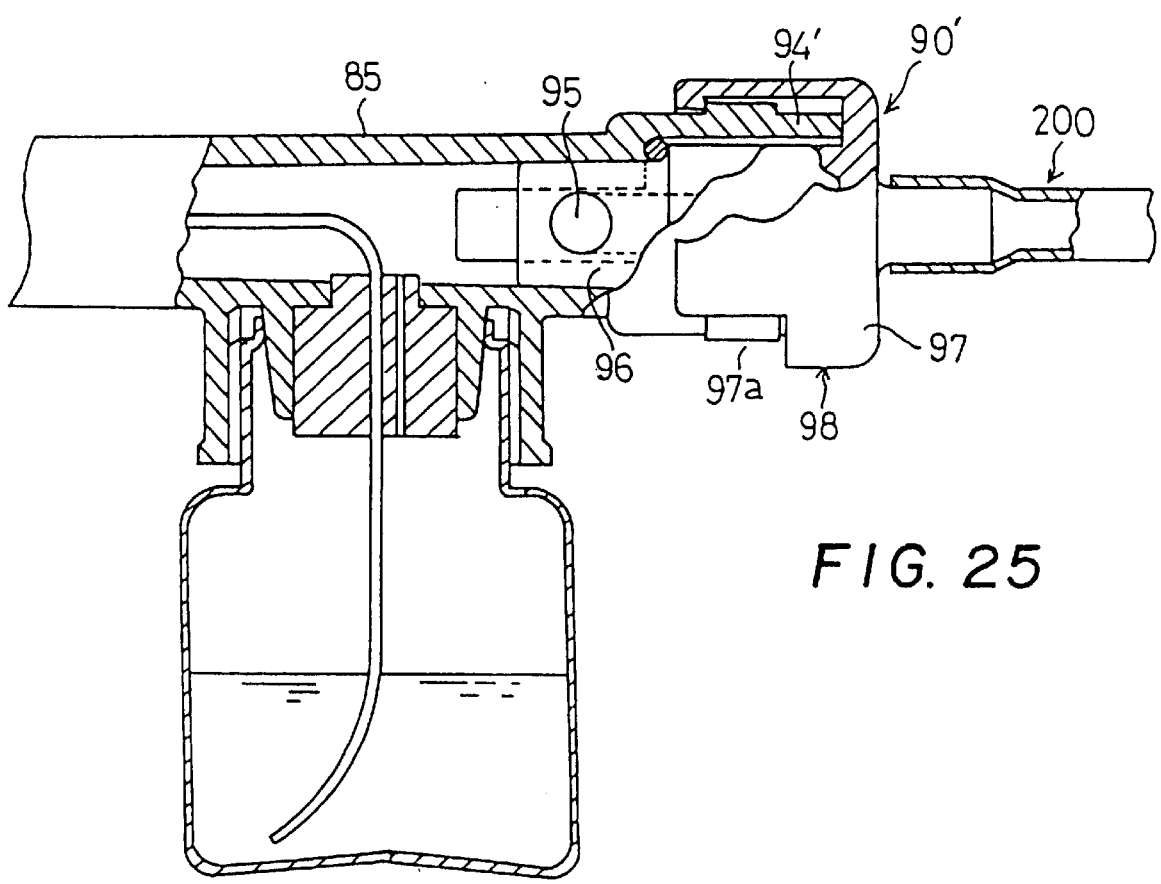
FIG. 25 is a side elevational view, partly in longitudinal cross-section, showing a structure of the fourth embodiment of the handy probe according to the present invention.
Figure 26:
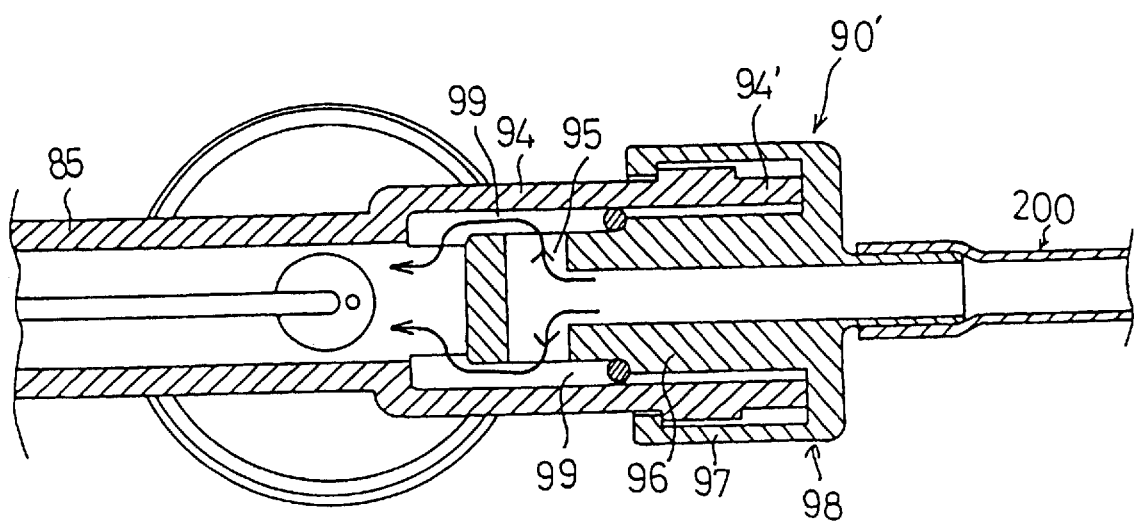
FIG. 26 is a plan view, in longitudinal cross-section, showing a structure of the fourth embodiment of the handy probe according to the present invention.

FIG. 22 illustrates the second embodiment of the periodontal pocket cleaning device according to the present invention, wherein the method of controlling the injection quantity of the atomized jet is modified. According to this embodiment, the injection nozzle 2B is provided with an opening 16 being formed in one part of its peripheral wall, and the feeding quantity of the compressed air is adjusted by means of the inlet air quantity regulating part 80 provided at the base end side of the cylindrical main body 85. In this cleaning device, injection and stoppage of the atomized jet can be controlled by opening and closing a perforated hole 16 with a finger tip. According to this method, when the hole 16 is closed, the atomized jet is ejected as usual, while on the other hand, when the hole 16 is opened, most of the compressed air, as fed into the compressed air guide passage 71 through the air feeding tube 200, is discharged outside from the hole 16, on account of which the air to be introduced into the liquid storage tank 50 and the air to be guided to the tip end side of the injection nozzle 2B are both rendered to be at a low pressure, to thereby enable the ejection of the atomized jet from the tip end of the injection nozzle 2B to be stopped instantaneously. This operation can, moreover, be carried out with a single hand and hence, the device is excellent in its operability. Incidentally, the illustrated embodiment of the cleaning device employs, in combination, the adjustment of the feed rate of the compressed air by means of the inlet air quantity regulating part 80, although this can be dispensed with. In this case, the adjustment of the jet-out quantity can be done, besides closing and opening of the hole 16, by controlling the degree of its opening with the finger tip.

FIG. 23 illustrates the third embodiment of the present invention, wherein an inlet air quantity regulating part 90, different from those as shown in FIGS. 4, 5, 6 and 22, is provided. This inlet air quantity regulating part 90 is to regulate the air-discharge quantity by forming an inner hole 91 at the base end side of the cylindrical main body 85, then notably fitting a ring member 93 from outside at the position where this inner hole 91 was formed, and adjusting the degree of overlapping between the above mentioned inner hole 91 and an outer hole 92 formed in the ring member 93. For example, as shown in FIG. 24(a), when the inner hole 91 and the outer hole 92 do not coincide, the holes 91, 92 are in a perfectly closed condition and hence, the discharge quantity of the atomized jet is at its maximum. Further, as shown in FIG. 24(b), when the inner hole 91 and the outer hole 92 are in a partly overlapped relationship, the compressed air is discharged outside, in part, with the consequence that the discharge quantity of the atomized jet becomes slightly less. Furthermore, as shown in FIG. 24(c), when the inner hole 91 and the outer hole 92 coincide perfectly, most of the compressed air, to be introduced through the air feeding tube 200, is discharged outside. Hence, discharge of the atomized jet is completely stopped. In this method too, discharge and stoppage of the atomized jet, as well as control of the discharge quantity thereof, can be done manually by one's own hand. By the way, as the shape of both inner hole 91 and the outer hole 92, various shapes may be adopted in addition to the illustrated example, such as a triangular-shaped hole, an oval-shaped hole, and further a truncated conical-shaped hole with the hole diameter being varied towards its depth.

FIGS. 25 to 28 illustrate the fourth embodiment of the present invention, wherein the structure of the inlet air quantity regulating part is modified. The inlet air quantity regulating part 90' is of such a construction that a bulged part 94, 94 is provided on the opposed position, at the base end side of the cylindrical main body 85, on and around the cylindrical part, and further that, at a position much closer to the base end side from the bulged part 94, an annular part 94' is continuously formed with an enlarged diameter, the outer diameter of which substantially coincides with the bulged part 94. Furthermore, the inlet air quantity regulating part 90' is of such a construction that a feed air regulating knob 98 of a double-cylinder structure, comprising an inner cylinder 96 which is traversed by a T-shaped passage 95, and an outer cylinder 97 with one part thereof being notched, are fitted on and around the base end of the cylindrical main body 85. By rotation of the feed air regulating knob 98, the compressed air, which has been sent in through the air feeding tube 200, is further sent into the cylindrical main body 85 of the handy probe 1 through a detour path 99 formed inside the bulged part 94 through the T-shaped passage 95.

FIGS. 27(*a*), 27(*b*) and 27(*c*) illustrate various modes of regulating the flow rate of the compressed air by means of the feed air regulating knob 98. For example, as shown in FIG. 27(*a*), in a state of the open end of the T-shaped passage 95 being positioned in the detour path 99, the flow rate of the compressed air reaches its maximum. On the other hand, as shown in FIG. 27(*b*), when a part of the open end of the T-shaped passage 95 is shielded, the flow rate of the compressed air is slightly reduced. Further, as shown in FIG. 27(*c*), in the case of the open end of the T-shaped passage 95 being completely closed, the feeding of the compressed air is totally stopped.

Figure 28:
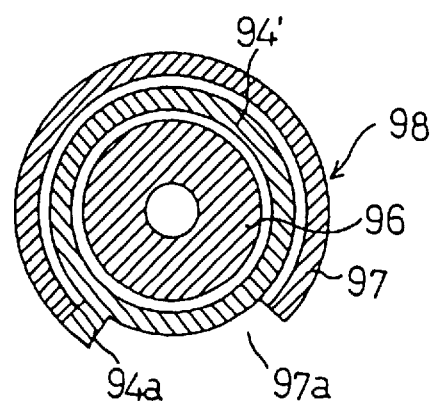
FIG. 28 is a cross-sectional view showing a rotation-regulating mechanism of air-feed control knob according to the fourth embodiment of the present invention.

By the way, the feed-air regulating knob 98 is so constructed that, as shown in FIG. 28, it is fitted on and around the outer periphery of the enlarged diameter annular part 94', and its rotational range is restricted by a stopper 94a projectively provided on the enlarged diameter annular part 94', which is engaged with a notched part 97a of an outer cylinder 97. When the inlet air quantity regulating part 90' of such construction is adopted, opening and closing of the flow passage for the compressed air is made possible with a small rotational angle, and its flow rate can also be regulated easily. With this mechanism, the number of constituent parts becomes reduced due to omission of the threaded screws and the plugs. Hence, the assembling steps can be kept to a minimum, which in turn contributes to the reduction in the manufacturing cost.

Figure 29:
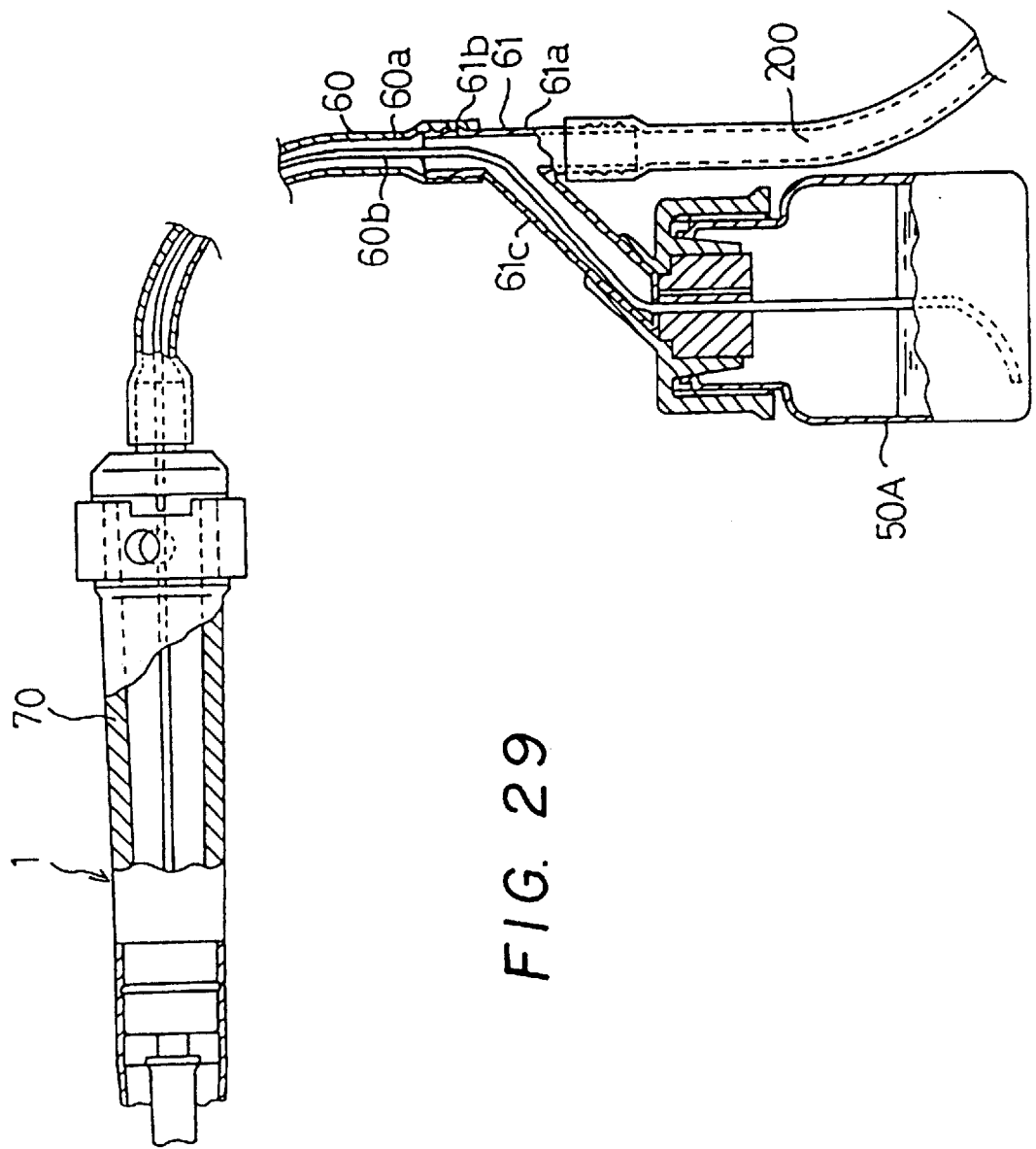
FIG. 29 is a side elevational view, in longitudinal cross-section, showing a structure of the fifth embodiment of the handy probe according to the present invention.

The first to fourth embodiments, which have so far been described in the foregoing, are for the cases, wherein the liquid storage tank 50 is integrally attached to the cylindrical body 70 of the handy probe 1, although the liquid storage tank 50 may be separate from the cylindrical body 70 of the handy probe 1, provided that the liquid storage tank 50 can be disposed in proximity to the cylindrical body 70 of the handy probe 1. The fifth embodiment of the present invention, shown in FIG. 29, is for a case, wherein the liquid storage tank 50 is separately provided from the cylindrical part 70 of the handy probe 1.

In this embodiment, a connecting tube 60 of a double-tube structure, wherein a liquid-feeding tube 60b is inserted into an air-feeding tube 60a, is led out of the cylindrical part 70 of the handy probe 1. The other end of the connecting tube 60 and the air-feeding tube 200 are joined together through a branched joint 61. A flexible tube may be used for the connecting tube 60, although a minimum possible hardness is required of the connecting tube 60 so that it may not be constricted, even when the liquid storage tank 50A is filled up with the liquid agent.

The branched joint 61 has a main pipe-line 61a to be connected to the air-feeding tube 200, a branch pipe-line 61b connected to the air-feeding tube 60a, and a branch pipe-line 61c connected to the liquid storage tank 50A. Into the branch pipe-line 61c, the liquid-feeding tube 60b is inserted and is led into the liquid agent within the liquid storage tank 50A. The compressed air, to be fed through the air-feeding tube 200, enters into the air-feeding tube 60a and at the same time, a part of the compressed air is also introduced into the liquid storage tank 50A through the branch pipe-line 61c to press the interface of the liquid agent in the interior of the liquid storage tank 50A, thereby pushing out the liquid agent into the handy probe 1 through the liquid-feeding tube 60b.

In this manner, when the liquid storage tank 50A is disposed at the nearest position to the cylindrical part 70 of the handy probe 1, without being integrally connected with the cylindrical part 70, weight-reduction of the cylindrical part 70 of the handy probe 1 can be realized. At the same time, since no liquid storage tank 50A is provided on the cylindrical part 70 of the handy probe 1, it can be easily gripped to improve the operability, with further possibility of reduction in diameter of the cylindrical part 70 of the handy probe 1. Moreover, whatever posture the handy probe 1 may take, the liquid storage tank 50A is maintained in a substantially vertical state due to the function of the flexible tube. Hence, stable feeding of the liquid agent, in the injection nozzle 2, through the liquid agent guide passage 10, can be secured. Also, since the liquid storage tank 50A is not in integral connection with the handy probe 1, it is easy to rotate the handy probe 1 around its axis. Therefore, even if the tip end part of the injection nozzle 2 is curved as shown in FIG. 19, the tip end of the injection nozzle 2 can be readily positioned at an arbitrary location such as a complicate innermost part of the oral cavity, and others.

Thus, in all of the first to fifth embodiments of the present invention as described in the foregoing, the handy probe 1 is devised so that injection and stoppage of the atomized jet, as well as adjustment of the jet-out quantity thereof, can be done by hand. Yet, such adjustment is not to electrically control the power source for the air pump 100, but rather to regulate the feed quantity of the compressed air to the injection nozzle 2 by either narrowing the flow path of the compressed air to restrict the flow rate of the compressed air, or by liberating the compressed air to regulate a feed quantity thereof to the injection nozzle. Such control means is safe, because no electrical wiring is required to be installed in the handy probe 1, which is liable to be wetted by the water drops, and yet the control is performed at a position closer to the injection nozzle 2, so that the response to the control operation is excellent.

The handy probe 1 has a construction as described in the foregoing. Now the air pump 100, which sends out the compressed air into the handy probe 1 through the air-feeding tube 200, will be explained. Various types of air pumps 100 can be used, but for the purpose of the present invention, the diaphragm type compressors are particularly well suited. Of the diaphragm type compressors, the type wherein the reciprocating vibratory body is used as the drive source for the diaphragm, in utilization of the repulsion and attraction functions of the electromagnets and the permanent magnets, is particularly well adapted for the purpose. The reason for employing a diaphragm type compressor is that no mechanical parts are exposed to the flow path of the air, so that clean air feeding can be secured. Also, the reason for employing the reciprocating vibratory body as the drive source is that, even when the jet-out quantity of the atomized jet is controlled by the closure of the flow path of the compressed air, as described in the first embodiment above, no load is imposed on the air pump 100, and also the jet-out pressure of the atomized jet does not become abnormally high.

In the present invention, since the liquid agent is stored in the liquid storage tank 50 attached to the handy probe 1, the jet-out pressure of the compressed air can be sufficiently low, and in particular, when the liquid agent is made to be pushed out of the liquid storage tank 50 by introducing a part of the compressed air into the liquid storage tank 50, the jet-out pressure of the compressed air can still be made lower to be sufficient for meeting the purpose. For example, a small sized and small capacity pump, of about 8 to 30 watts in its power consumption, can sufficiently serve the intended purpose. This constitutes a remarkable contrast to the conventional periodontal pocket cleaning device using the jet water current, which requires the power consumption of about 30 to 50 watts.

Figure 30:
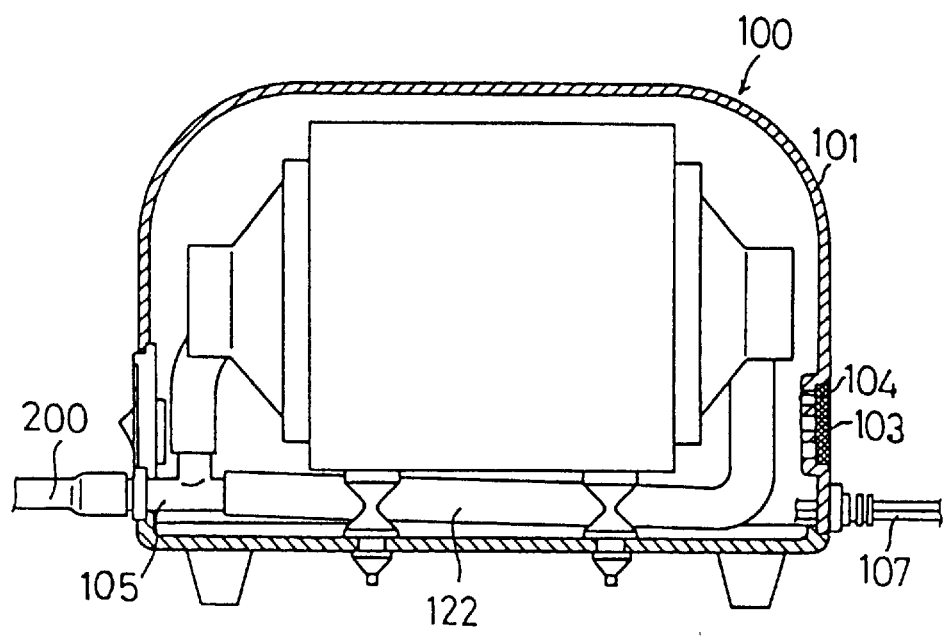
FIG. 30 is a side-elevational view, partly in longitudinal cross-section, showing the diaphragm type compressor.
Figure 31:
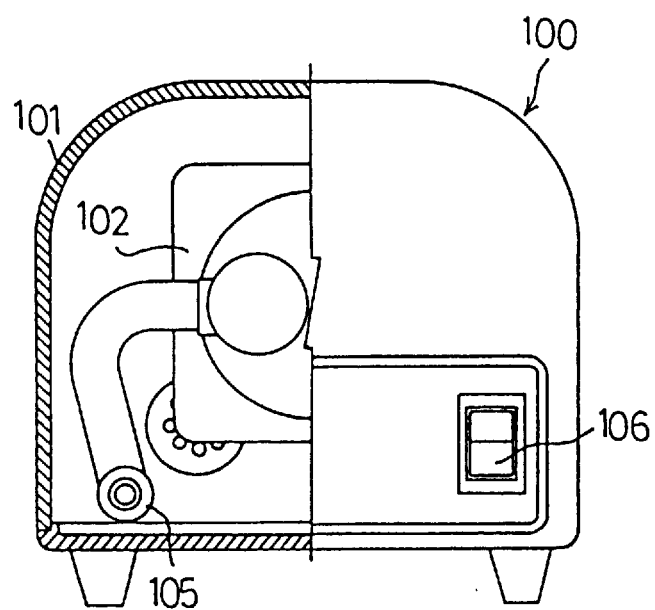
FIG. 31 is a front view, partly in transverse cross-section, showing the diaphragm type compressor.
Figure 32:
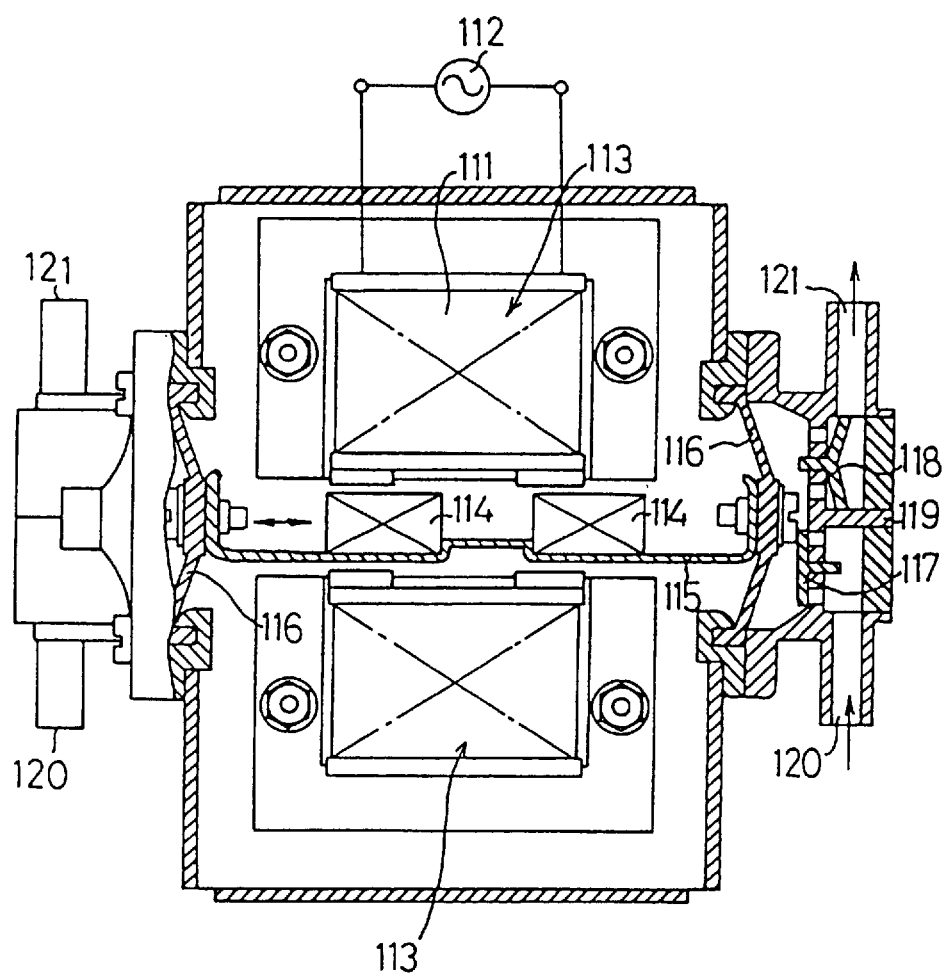
FIG. 32 is an explanatory diagram, partly in cross-sectional view, showing a main body of the compressor.

FIGS. 30 to 32 illustrate the diaphragm type compressor, wherein: FIG. 30 is a side elevational view with its outer casing being cut away to show its interior; FIG. 31 is a front elevational view with its outer casing being cut away in part to show its interior; and FIG. 32 is a plan view, partly in cross-section, of the compressor main body. This diaphragm type compressor is of such a construction that the compressor main body 102 is housed in a sound-proof outer casing 101, and an air-inlet port 104 is formed at one lateral part of the casing 101, with an air filter 103 being disposed in front of the inlet port 104. The outer casing 101 is traversed by an outlet tube 105 of the compressor main body 102, and the air-feeding tube 200 is connected to the outlet tube 105. In the drawing, a reference numeral 106 designates a power source switch, and a numeral 107 refers to a power source wire.

The internal structure of the compressor main body 102 is shown in FIG. 32. That is to say, this compressor main body 102 is of such a construction that: a pair of electromagnets 113, 113, made by connecting an alternating current (AC) power source 112 to an electric winding 111, are disposed in mutually opposed positions; that a pair of permanent magnets 114, 114, each of which is magnetized in the north (N) or the south (S) pole, are arranged in the space between the electromagnets 113, 113 along the longitudinal direction of the space, and fixed to a slidable rod 115; diaphragms 116, 116 are mounted on both ends of the rod 115; and, in opposition to each of the diaphragms 116, 116, an inlet valve 117 and an outlet valve 118 are attached. Both inlet valve 117 and outlet valve 118 are isolated by placing a partition 119 between them, and an inlet port 120 is formed at the side of the inlet valve 117, while an outlet port 121 is formed at the side of the outlet valve 118, whereby the compressed air discharged from the outlet port 121 of each of the two diaphragms 116, 116 is made to flow together by a confluent pipe 122, as shown in FIG. 30. By the way, there is no illustration of various structural components including the inlet valve 117, the outlet valve 118, and so forth to be provided in correspondence to the diaphragm 116 at the left side of FIG. 32. Such structural components are exactly the same as those to be provided in correspondence to the diaphragm 116 at the right side of the drawing.

In this illustrated embodiment, a pair of mutually opposed electro-magnets 113, 113 are used, although such electro-magnet can be provided at one side alone. Also, it may be feasible to adopt a construction (not shown) wherein annular electromagnets, each having a hollow part therein, are disposed in series like solenoid plungers, and a rod, with a permanent magnet being attached thereon, is caused to pass through the hollow part, and then the diaphragms 116, 116 are attached onto both ends of the rod.

In such a diaphragm type compressor, when alternating current (AC) voltage is applied to a winding 111 thereof, to bring about the magnetic field reversing phenomenon, within the electromagnet 113, in synchronism with the polarity reversal of the power source frequency, the permanent magnets 114, 114 perform their attraction and repulsion functions in correspondence to the magnetic field reversal. This operation of the permanent magnets is performed in the form of the reciprocating motion of the rod 115 which vibrates the diaphragm 116, thereby sending out the compressed air.

In the compressor main body 102, when the flow rate of the compressed air is reduced at an intermediate part of the compressed air guide passage 71 of the handy probe 1, with a view to controlling injection and stoppage of the atomized jet, as well as its jet-out quantity, as is the case with the first embodiment, a decrease in the vibration amplitude of the diaphragm takes place, as well as a decrease in the vibration amplitude of the permanent magnets 114, 114, without any possibility of an accompanying generation of excess current. Rather, the operating load of the compressor becomes lessened, and the power consumption decreases accordingly. Also, by liberating the compressed air, as is the case with the second and the third embodiments, such a diaphragm type compressor can, of course, be utilized for the periodontal pocket cleaning device, in which the control is performed on the jet-out quantity of the atomized jet. With such a diaphragm type compressor, a method of directly controlling the flow rate of the compressed air within the handy probe 1 as mentioned in the foregoing can be adopted, other than the ordinary method of controlling the electrical system for the regulation of the jet-out quantity of the atomized jet. Hence, the excellent operability of the cleaning device can be exhibited.

Figure 33A:
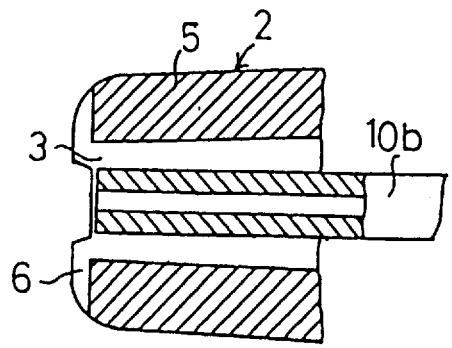
FIG. 33(a) is an explanatory diagram, in longitudinal cross-section, showing another embodiment of the injection nozzle.
Figure 33B:
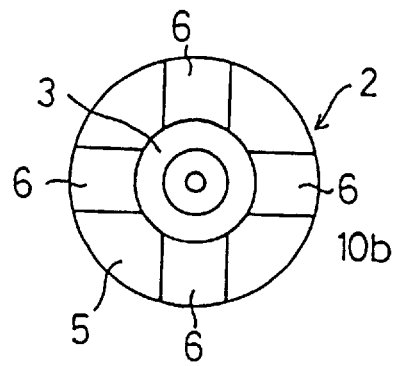
FIG. 33(b) is an explanatory diagram showing a modified embodiment of the jet-out port, as viewed from a front thereof.
Figure 34:
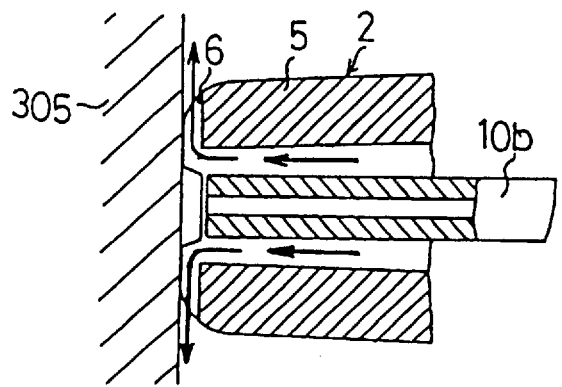
FIG. 34 is an explanatory diagram showing a state of the tip end of the injection nozzle, when it is in contact with the tooth gum.
Figure 35:
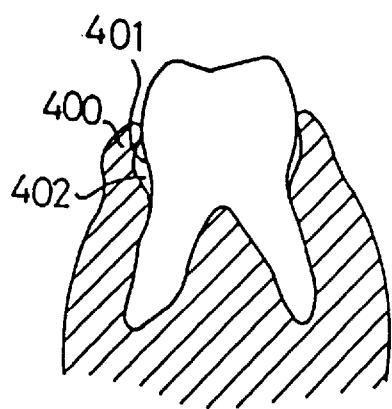
FIG. 35 is an explanatory diagram showing a forming position of the periodontal pocket.

One of the advantages derived from use of the diaphragm type compressor, which employs the reciprocating vibratory body therein, is that, even if a situation takes place such that the tip end of the injection nozzle 2 comes into contact with the tooth gum 305 (or gingiva) to restrict the jet-out quantity of the air, the atomized jet does not get an abnormally high pressure, as already mentioned in the foregoing. Needless to say, other methods can also be contemplated for avoiding an abnormal increase in the pressure of the atomized jet, in case the tip end of the injection nozzle 2 comes into contact with the tooth gum 305. For example, an improved structure may be devised for the tip end of the injection nozzle 2, as shown in FIGS. 33(a) and 33(b). That is to say, by forming grooves 6, 6, 6, 6 in the mutually crossing directions, as shown in FIGS. 33(a) and 33(b), it becomes possible to cause the atomized jet to escape laterally via the grooves 6, 6, 6, 6, even when the atomized jet hits the surface of the tooth gum 305 and a surrounding region thereof, as shown in FIG. 34. Therefore, when the injection nozzle 2 of such construction is employed, there is no risk of the atomized jet attaining an abnormally high jet-out pressure, even in the case where ejection of the atomized jet from the injection nozzle 2 is restricted, with the consequence that, even when the injection nozzle 2 is abruptly brought to the proximity of the tooth gum 305, or the injection nozzle 2 is brought into contact with the tooth gum 305, there is no possibility of the atomized jet vigorously hitting against the tooth gum 305, but rather blows softly onto it.

INDUSTRIAL APPLICABILITY

The periodontal pocket cleaning device according to the present invention functions to push open the gingiva which firmly closes the entrance of the periodontal pocket, by ejection from the injection nozzle of the atomized jet consisting of a large amount of compressed air blown out at a rate of 2 to 30 l/min. and a small amount of liquid agent, such as water or liquid chemicals, dispersed in an atomized form. This causes the compressed air to penetrate into the periodontal pocket to kill the periodontal pathogenic fungi with oxygen contained in the compressed air and at the same time, to prevent the oral cavity from being dried up with use of the liquid chemicals as the liquid agent, accompanied by further pharmaceutical efficacy, such as disinfecting effect, quenching effect, dental plaque dissolving effect, dental caries preventive effect, dental calculus build-up preventive effect, anastaltic effect, perception allergy preventive effect, anesthetic effect, and so forth.

The atomized jet, to be ejected from the periodontal pocket cleaning device according to the present invention, consists mainly of the compressed air and hence, has a low fluid viscosity. On account of this, even when such atomized jet cannot penetrate into the periodontal pocket to be cleaned, a part of the atomized jet, which has splashed back at the tooth surface, etc., turns its direction and becomes able to penetrate again into the aimed periodontal pocket or other periodontal pocket, so that there is no stringent requirement for the positioning of the injection nozzle within the oral cavity. Hence, the device can be used with much convenience.

Further, the periodontal pocket cleaning device according to the present invention has a small jet-out quantity of the liquid agent, and yet the liquid agent per se is either stored in the liquid storage tank, which is integrally attached to the cylindrical part of the handy probe, or is disposed in proximity to the cylindrical part of the handy probe 1, with the consequence that the liquid agent can be atomized with the compressed air having a jet-out pressure of as low as 0.05 to 0.80 $kg/cm^2$. Accordingly, a small-sized air pump can be used, which will lead to the size-reduction of the cleaning device as a whole and reduction in the manufacturing cost of the same. Further, in view of the fact that the periodontal pocket cleaning device, according to the present invention, has a small jet-out pressure of the compressed air, there is no apprehension whatsoever as to injury to be caused to the delicate and sensitive inner wall of the periodontal pocket.

Furthermore, since the liquid agent is incorporated in the handy probe, there is no difference in the atomized condition of liquid to take place depending on the height of the handy probe, as is the case with the conventional handy probe where water stored in the device main body separates from the handy probe is to be sucked up through a lengthy tube. Hence, the atomized jet can be generated stably without regard to the height level of the handy probe.

In addition, since the quantity of use of the liquid agent with the periodontal pocket cleaning device, according to the present invention, is extremely small, there is no possibility of the liquid agent overflowing from the mouth, nor is there a necessity for frequently disgorging the water accumulated in the oral cavity. Hence, the device is conveniently and advantageously used at any place, other than the wash basin, such as, for example, a bedside, without limitation to the place of its use.

When a part of the compressed air is branched out into an inner space of the liquid storage tank to press the liquid surface of the liquid agent in the liquid storage tank, a push-out function is exerted on the liquid agent, wherein the push-out function cooperates with the suction function of the liquid agent, due to the pressure-reduction at the tip end part of the nozzle, to assist the discharge of the liquid agent. Accordingly, in this case, the jet-out pressure of the compressed air can be made much lower and at the same time, a stable atomized jet can be generated even at a lower jet-out pressure. Since the compressed air is introduced into the liquid storage tank, the evacuation phenomenon, within the liquid storage tank due to suction of the liquid agent, can be avoided. Hence, there is no difficulty in drawing out the liquid agent by suction, even if its quantity becomes small, and the liquid agent can be sucked out with stability. Also, since no vacuum is created in the interior of the liquid storage tank, there is no necessity for providing the liquid storage tank with an opening for introduction of outside air, with the result that perfect air-tight closure of the liquid storage tank is made possible, and no risk of liquid leakage takes place, even when the liquid storage tank falls down.

Further, when the liquid storage tank is connected by the connecting tube, with the cylindrical part of the handy probe at the proximal position of the cylindrical part of the handy probe, without its being integrally combined with the cylindrical part of the handy probe, it becomes easier to grip the handy probe, because the liquid storage tank is not present at the cylindrical part of the handy probe and at the same time, reduction in diameter of the cylindrical part of the handy probe becomes possible. Further, since the liquid storage tank is capable of maintaining its definite posture even in case the handy probe takes various postures, the liquid agent can be stably supplied to the injection nozzle through the liquid agent guide passage. Hence, the handy probe has its improved operating efficiency, and is able to bring the tip end of the injection nozzle, relatively easily, to any complicated position, such as, for instance, in the innermost part of the oral cavity.

Furthermore, if the effective area of the air jet-out part at the injection port is in a range of from 0.5 $mm^2$ to 20 $mm^2$, the jet-out pressure becomes more stabilized in the predetermined range, whereby generation of atomized jet of a preferred quality is secured.

Moreover, in case the wind pressure, at a spot 5 mm distant from the injection port in the axial direction of the injection nozzle, is set to be 1~10 $g/\pi \cdot (5 \text{ mm})^2$, an appropriate feel during use can be obtained without causing injury to the inner wall of the delicate and sensitive periodontal pocket.

In addition, a portion of the liquid agent guide passage to be positioned at the injection port of the handy probe is made of a tube having flexibility, the automatic centering function is exhibited to enable the flexible tube to be constantly positioned at the center of the injection port, whereby ejection of the atomized jet having uniform diameter of the atomized articles can be secured.

Still further, when the tip end position of the flexible tube is in a range of ±2 mm in the axial direction of the injection nozzle, the automatic centering function of the flexible tube can be more stably exhibited, with the consequence that, the atomized jet with uniform particle size can be obtained.

Still more, when the air pump is the diaphragm type compressor, and the drive source for the diaphragm is the reciprocating vibratory body which utilizes the repulsion and attraction function of the electromagnets and the permanent magnets, clean compressed air can be sent into the handy probe, since the air passageway and the drive mechanism are perfectly isolated.

Also, the jet-out quantity of the atomized jet can be freely controlled at the hand of a user who is operating the handy probe, in the case of providing means for regulating the flow rate of the compressed air at an intermediate part of the air-feeding tube for supplying the compressed air from the air pump to the handy probe, or at an intermediate part of the compressed air guide passage of the handy probe, or in the case of providing means for discharging the compressed air to the outside at an intermediate part of the air-feeding tube for supplying the compressed air to the handy probe from the air pump, or at an intermediate part of the compressed air guide passage of the handy probe. Yet, since the control operation is done at the hand of the operator, the response to the control operation is high. Moreover, since the control means is not operated by an electrical system, it is suited for control of the jet-out quantity of the atomized jet from the handy probe which is liable to be wetted with water, and so forth.

Even when the flow rate of the atomized jet is controlled by regulating, in particular, the flow rate of the compressed air, if and when the diaphragm type compressor with the reciprocating vibratory body being provided as the drive source, which utilizes the repulsion and attraction functions of the electromagnets and the permanent magnets, is used, such flow rate regulation of the compressed air does not amount to an increase in the operational load to the diaphragm type compressor. Hence, there is not a possibility of either an increase in the power consumption or a burning of the compressor will take place.

In another aspect, even if the feeding of the compressed air to the handy probe is regulated, or even if, during use of the handy probe, the jet-out quantity of the atomized jet is restricted by the tip end part of the injection nozzle coming into contact of with the tooth gum, owing to which the jet-out quantity of the atomized jet is limited, there is no apprehension of the jet-out pressure of the atomized jet becoming abnormally high, so that the handy probe can be used with safety.

In case the nozzle part is made separable from the main body of the handy probe, or the intra-nozzle liquid conduit pipe is made separable from the main body of the handy probe, even if a situation should take place such that the nozzle part or the tip end part of the intra-nozzle liquid conduit pipe comes into contact with the oral cavity, during operation of the pocket cleaning device, there is no risk of infection due to the pathogenic fungi if the nozzle part or the intra-nozzle liquid conduit pipe as used by another person is discarded and replaced with a new one or with one already used by the same user. In this way, any possibility of infection due to pathogenic fungi in the hospital can be prevented. Further, depending on necessity, the mode of injection of the nozzle part can be varied in correspondence to variations in the position of the oral cavity to be injected by replacement of the nozzle part with one having different length and shape. Also, by changing the inner diameter of the intra-nozzle liquid conduit pipe, the jet-out quantity of the liquid agent can be varied.

Furthermore, when the periodontal pocket cleaning device is delivered to the customer with the injection nozzle and the intra-nozzle liquid conduit pipe being integrally connected together in advance, replacement of the injection nozzle, as well as the intra-nozzle liquid conduit pipe, can be carried out simultaneously by the customer. As the consequence, there is no necessity for accurately positioning the intra-nozzle liquid conduit pipe at a predetermined position within the injection nozzle, at the time of replacing the same, whereby the replacement work of the injection nozzle and the intra-nozzle liquid conduit pipe by the user himself or herself becomes simple and easy. Moreover, since the intra-nozzle liquid conduit pipe can be set in advance within the injection nozzle at the manufacturer's side for delivery of the cleaning device to the customers, high precision assembly is possible and the stabilized injection of the atomized jet can be ensured.

Although the present invention has been described with reference to particular embodiments, it will be understood by those skilled in the art that the invention is capable of a variety of alternative embodiments within the spirit and scope of the invention as recited in the appended claims.

We claim:

1. In a periodontal pocket cleaning device including a handy probe provided with an air-jet ejection mechanism, an air pump for producing compressed air, and an air-feeding tube for feeding said compressed air from said air pump to said handy probe, an improved handy probe comprising:

an injection nozzle located at a first end of said handy probe, wherein said injection nozzle at said first end of said handy probe includes a jet-out port provided at a tip end of said injection nozzle and wherein a second end of said handy probe is connected to said air-feeding tube leading from said air pump of said periodontal pocket cleaning device;

a liquid storage tank for storing a liquid agent therein, wherein said liquid agent is any one of water and liquid chemicals, and wherein said liquid storage tank is suspendedly attached to said handy probe at an intermediate position between said injection nozzle at said first end of said handy probe and said second end of said handy probe where said air-feeding tube of said periodontal pocket cleaning device is attached to said handy probe;

a liquid agent guide passage for guiding said liquid agent in said liquid storage tank to a substantially center position of said jet-out port via said injection nozzle; and a compressed air guide passage for guiding said compressed air to a position which surrounds said liquid agent guide passage at said jet-out port via said injection nozzle, wherein a jet-out pressure of said compressed air to be ejected from said injection nozzle is set in a range of from 0.05 to 0.80 $kg/cm^2$, a jet-out quantity of said compressed air is set in a range of from 2 to 30 l/min., and a jet-out quantity of said liquid agent is set in a range of from 1 to 10 cc/min.

2. The periodontal pocket cleaning device as set forth in claim 1, wherein said liquid agent guide passage is constructed with a liquid agent feeding tube for leading said liquid agent from said liquid storage tank to an introduction part of said injection nozzle, and an intra-nozzle liquid conduit pipe for guiding said liquid agent up to said substantially center position of said jet-out port by coaxially passing through an internal space of said injection nozzle with respect to an outer cylinder of said injection nozzle; and said compressed air passage is constructed with an extra-nozzle air feeding passage which leads said compressed air fed from outside into said introduction part of said injection nozzle, and an intra-nozzle air feeding passage which leads said compressed air, as introduced, into said injection nozzle to said jet-out port in a manner to coaxially surround said intra-nozzle liquid conduit pipe.

3. The periodontal pocket cleaning device as set forth in any one of claim 1 and 2, wherein said compressed air guide passage is branched out to form at least two branched-out compressed air guide passages, and a first of said at least two branched-out compressed air guide passages is led to said injection nozzle, and a second of said at least two branched-out compressed air guide passages is led into said internal space of said liquid storage tank.

4. The periodontal pocket cleaning device as set forth in any one of claims 1 and 2, wherein said liquid storage tank is integrally connected with said cylindrical part of said handy probe associated with said injection nozzle.

5. The periodontal pocket cleaning device as set forth in any one of claims 1 and 2, wherein said cylindrical part of said handy probe associated with said injection nozzle and said liquid storage tank are connected by means of a connecting tube which is led out of said cylindrical part of said handy probe.

6. The periodontal pocket cleaning device as set forth in any one of claims 1 and 2, wherein an effective area of said air jet-out part at said injection port, except for said liquid agent guide passage, is in a range of from 0.5 mm² to 20 mm².

7. The periodontal pocket cleaning device as set forth in any one of claims 1 and 2, wherein a wind pressure at a spot 5 mm distant from said jet-out port along a axial direction of said injection nozzle is in a range of 1–10 g/π•(5 mm)².

8. The periodontal pocket cleaning device as set forth in any one of claims 1 and 2, wherein a part of said liquid agent guide passage to be positioned, at least, at said injection port of said handy probe is constituted with a flexible tube.

9. The periodontal pocket cleaning device as set forth in claim 8, wherein a position of said tip end of said flexible tube to be positioned at an open center position of said injection port is in a range of ±2 mm in said axial direction of said nozzle with respect to said open end position of said outer cylinder of said nozzle.

10. The periodontal pocket cleaning device as set forth in any one of claims 1 and 2, wherein said air pump is a diaphragm type compressor, and a drive source for said diaphragm is a reciprocating vibratory body utilizing a repulsion function and an attraction function of both electromagnets and permanent magnets.

11. The periodontal pocket cleaning device as set forth in claim 10, wherein means for regulating a flow rate of said compressed air is provided at anyone of an intermediate part of said compressed air guide passage for said handy probe, and at an intermediate part of said air feeding tube to feed said compressed air from said air pump into said handy probe.

12. The periodontal pocket cleaning device as set forth in claim 10, wherein means for discharging a part of said compressed air to any one of outside of said compressed air guide passage and outside of said air feeding tube is provided at any one of an intermediate part of said compressed air guide passage for said handy probe, and at an intermediate part of said air feeding tube to feed said compressed air from said air pump to said handy probe.

13. The periodontal pocket cleaning device as set forth in any one of claims 1 and 2, wherein said injection nozzle is separable from a main body of said handy probe.

14. The periodontal pocket cleaning device as set forth in claim 13, wherein said injection nozzle and said intra-nozzle liquid conduit pipe are integrally fixed in advance.

15. The periodontal pocket cleaning device as set forth in any one of claims 1 and 2, wherein said intra-nozzle liquid conduit pipe is separable from a main body of said handy probe.

16. In a periodontal pocket cleaning device including a handy probe provided with an air-jet ejection mechanism, an air pump for producing compressed air, and an air-feeding tube for feeding said compressed air from said air pump to said handy probe, an improved handy probe comprising:

an injection nozzle with a jet-out port being provided at a tip end thereof;

a liquid storage tank for storing therein liquid agent containing any one of water and liquid chemicals;

a liquid agent guide passage for guiding said liquid agent in said liquid storage tank to a substantially center position of said jet-out port via said injection nozzle;

a compressed air guide passage for guiding said compressed air to a position which surrounds said liquid agent guide passage at said jet-out port via said injection nozzle, wherein a jet-out pressure of said compressed air to be ejected from said injection nozzle is set in a range of from 0.05 to 0.80 kg/cm², a jet-out quantity of said compressed air is set in a range of from 2 to 30 l/min., and a jet-out quantity of said liquid agent is set in a range of from 1 to 10 cc/min.;

wherein said liquid agent guide passage is constructed with a liquid agent feeding tube for leading said liquid agent from said liquid storage tank to an introduction part of said injection nozzle, and an intra-nozzle liquid conduit pipe for guiding said liquid agent up to said substantially center position of said jet-out port by coaxially passing through an internal space of said injection nozzle with respect to an outer cylinder of said injection nozzle; and said compressed air passage is constructed with an extra-nozzle air feeding passage which leads said compressed air fed from outside into said introduction part of said injection nozzle, and an intra-nozzle air feeding passage which leads said compressed air, as introduced, into said injection nozzle to said jet-out port in a manner to coaxially surround said intra-nozzle liquid conduit pipe; and wherein said compressed air guide passage is branched out to form at least two branched-out compressed air guide passages, and a first of said at least two branched-out compressed air guide passages is led to said injection nozzle, and a second of said at least two branched-out compressed air guide passages is led into said internal space of said liquid storage tank.

17. In a periodontal pocket cleaning device including a handy probe provided with an air-jet ejection mechanism, an air pump for producing compressed air, and an air-feeding tube for feeding said compressed air from said air pump to said handy probes an improved handy probe comprising;

an injection nozzle with a jet-out port being provided at a tip end thereof;

a liquid storage tank for storing therein liquid agent containing any one of water and liquid chemicals;

a liquid agent guide passage for guiding said liquid agent in said liquid storage tank to a substantially center position of said jet-out port via said injection nozzle;

a compressed air guide passage for guiding said compressed air to a position which surrounds said liquid agent guide passage at said jet-out port via said injection nozzle, wherein a jet-out pressure of said compressed air to be ejected from said injection nozzle is set in a range of from 0.05 to 0.80 kg/cm², a jet-out quantity of said compressed air is set in a range of from 2 to 30 l/min., and a jet-out quantity of said liquid agent is set in a range of from 1 to 10 cc/min.; and wherein said compressed air guide passage is branched out to form at least two branched-out compressed air guide passages, and a first of said at least two branched-out compressed air guide passages is led to said injection nozzle, and a second of said at least two branched-out compressed air guide passages is led into an internal space of said liquid storage tank.

* * * * *